United States Patent
Choi et al.

(10) Patent No.: US 11,142,777 B2
(45) Date of Patent: Oct. 12, 2021

(54) METHOD FOR PREPARING MUTANT STRAIN HAVING HIGH PRODUCIBILITY OF PHYTOENE AND MUTANT STRAIN PREPARED THEREBY

(71) Applicant: UNIVERSITY OF SEOUL INDUSTRY COOPERATION FOUNDATION, Seoul (KR)

(72) Inventors: Yong Jun Choi, Seoul (KR); Sun Wook Jeong, Daejeon (KR); Jua Kim, Seoul (KR); Eunkyung Hong, Goyang-si (KR); Kwang Jin Cho, Seoul (KR)

(73) Assignee: University of Seoul Industry Cooperation Foundation, Seoul (KR)

( * ) Notice: Subject to any disclaimer, the term of this patent is extended or adjusted under 35 U.S.C. 154(b) by 0 days.

(21) Appl. No.: 16/498,269

(22) PCT Filed: Mar. 29, 2018

(86) PCT No.: PCT/KR2018/003725
§ 371 (c)(1),
(2) Date: Sep. 26, 2019

(87) PCT Pub. No.: WO2018/182334
PCT Pub. Date: Oct. 4, 2018

(65) Prior Publication Data
US 2020/0102579 A1 Apr. 2, 2020

(30) Foreign Application Priority Data
Mar. 30, 2017 (KR) ........................ 10-2017-0040806

(51) Int. Cl.
C12N 15/90 (2006.01)
C12N 9/12 (2006.01)
C12N 15/74 (2006.01)
C12P 5/02 (2006.01)
C12N 1/20 (2006.01)
C12R 1/01 (2006.01)

(52) U.S. Cl.
CPC ........... *C12N 15/902* (2013.01); *C12N 1/205* (2021.05); *C12N 9/1241* (2013.01); *C12N 15/74* (2013.01); *C12P 5/026* (2013.01); *C12N 2800/30* (2013.01); *C12R 2001/01* (2021.05)

(58) Field of Classification Search
None
See application file for complete search history.

(56) References Cited

U.S. PATENT DOCUMENTS 5,684,238 A 11/1997 Ausich et al.

FOREIGN PATENT DOCUMENTS

KR 10-2011-0032375 3/2011

OTHER PUBLICATIONS

Jeong et al., "Metabolic Engineering of *Deinococcus radiodurans* for the Production of Phytoene," *J Microbiol Biotechnol* 28(10): 1691-1699, 2018 (Abstract only).
Jeong et al., "Development of Cre-lox based multiple knockout system in *Deinococcus radiodurans*R1," *Korean J Chem Eng* 34: 1728-1733, 2017 (Abstract only).
Zhang et al., "Knockout of crtB or crtI gene blocks the carotenoid biosynthetic pathway in *Deinococcus radiodurans*R1 and influences its resistance to oxidative DNA-damaging agents due to change of free radicals scavenging ability," *Arch Microbiol* 188: 411-419, 2007 (Abstract only).
Meima and Lidstrom "Characterization of the Minimal Replicon of a Cryptic *Deinococcus radiodurans* SARK Plasmid and Development of Versatile *Escherichia coli-D. radiodurans* Shuttle Vectors" *Applied and Environmental Microbiology* 66(9):3856-3867 (2000).
Satoh et al. "Down-regulation of radio resistance by LexA2 in *Deinoccoccus radiodurans*" *Microbiology* 152:3217-3226 (2006).
Xu et al. "Identification and functional analysis of a phytoene desaturase gene from the extremely radioresistant bacterium *Deinoccoccus radiodurans*" *Microbiology* 153:1642-1652 (2007).
Nguyen et al. "The essential histone-like protein HU plays a major role in *Deinococcus radiodurans* nucleoid compaction" *Molecular Microbiology* 73(2):240-252 (2009).
Tian and Hua "Carotenoid biosynthesis in extremophilic *Deinococcus-Thermus* bacteria" *Trends in Microbiology* 18(11): 512-520 (2010).
"*Deinococcus radiodurans* R1 chromosome 1, complete sequence" GenBank: CP015081.1 (2016).
Jeong et al., "Development of Cre-lox based multiple knockout system in *Deinococcus radiodurans* R1," *Korean J Chem Eng*, DOI: 10.1007/s11814-017-0082-5, pp. 1-6, 2017.
Satoh et al., "Development of versatile shuttle vectors for *Deinococcus grandis*," *Plasmid* 62:1-9, 2009.

*Primary Examiner* — Kagnew H Gebreyesus
(74) *Attorney, Agent, or Firm* — Klarquist Sparkman, LLP

(57) ABSTRACT

The present invention relates to a method for preparing a mutant strain having high producibility of phytoene and a mutant strain prepared thereby. More particularly, a *Deinococcus radiodurans* mutant strain, prepared by the method of the present invention, having high producibility of phytoene, does not retain an artificial antibiotic-resistant gene, although constructed by introducing a metabolism engineering method, and has high producibility of phytoene. Thus, the mutant strain prepared according to the method can find useful applications in the mass production of phytoene.

17 Claims, 19 Drawing Sheets
Specification includes a Sequence Listing.

METHOD FOR PREPARING MUTANT STRAIN HAVING HIGH PRODUCIBILITY OF PHYTOENE AND MUTANT STRAIN PREPARED THEREBY

CROSS REFERENCE TO RELATED APPLICATIONS

This is the U.S. National Stage of International Application No. PCT/KR2018/003725, filed Mar. 29, 2018, which in turn claims the benefit of Korean Application No. 10-2017-0040806, filed Mar. 30, 2017, both of which applications are herein incorporated in their entirety.

BACKGROUND OF THE INVENTION

1. Field of the Invention

The present invention relates to a method for preparing a mutant strain having high producibility of phytoene and a mutant strain prepared thereby.

2. Description of the Related Art

Microbial metabolic engineering is a technique to improve the genome of a microorganism to utilize for the desired purpose. Useful metabolites can be obtained from genetic information and metabolic circuits of microorganisms. Microbial gene manipulation techniques trigger the development of more useful metabolites and the techniques to improve characteristics of the useful metabolites. In particular, site-specific recombination techniques such as Flp/FRT and cre/lox in metabolic engineering can be applied to various life models including plants, yeast and microorganisms.

It is known that *Deinococcus radiodurans* is resistant to ionizing radiation, which can directly damage DNA or protein of an organism. This strain is able to repair DNA damage caused by ionizing radiation in a short time and can eliminate efficiently reactive oxygen species (ROS) generated in cells by enzymatic or non-enzymatic systems. Due to such characteristics, *Deinococcus radiodurans* is used for the purification of radioactive waste. In addition, it is expected that the cases of useful applications of *Deinococcus radiodurans* are increasing in various fields including medicine, health care and biotechnology.

According to the reports up to date, techniques for producing a mutant strain by introducing genes of other microorganisms into cells or using homologous recombination methods have been developed for the metabolic control of *Deinococcus radiodurans*. However, such techniques for producing a mutant strain are not only time-consuming due to the repeated gene cloning process but also have difficulty in producing multiple mutant strains due to the limitation of antibiotic markers for selecting mutant strains.

On the other hand, carotenoid is a C-40 isoprenoid compound having antioxidant activity, which is a general term for a kind of pigment distributed widely in the natural world. There are over 600 kinds of carotenoids known to date, each of which is in a different form. Recently, genes encoding enzymes involved in carotenoid biosynthesis have been studied. As a result, genes and cDNAs encoding enzymes involved in many carotenoid biosynthesis have been identified in bacteria, algae, strains and higher plants such as tobacco, tomato and pepper. Due to the importance of carotenoids, studies on genes encoding enzymes involved in carotenoid biosynthesis have been on the spot light.

Phytoene, one of carotenoids, is known as an effective ingredient for skin whitening, so that it can be used as a UV absorber, an antioxidant and an anti-inflammatory agent.

In relation to the above, Korean Patent No. 10-0813284 describes that the production of carotenoid components is increased by continuously expressing citrus phytoene biosynthetic enzyme (PSY) genes in the rapeseed plant transformed by agrobacterium-transformation method.

Accordingly, the present inventors have been tried to construct a *Deinococcus* species strain having high producibility of phytoene by using metabolic engineering methods. In the course of our study, the present inventors constructed a mutant strain of *Deinococcus radiodurans* having deletion of DR0861 gene, a mutant strain of *Deinococcus radiodurans* having deletion of DR0861 gene but overexpresing DR0862, DR1087, DR1395 or DR1475 gene, and a mutant strain of *Deinococcus radiodurans* having deletion of DR0861 and DR2250 genes but over-expressing DR0862 and DR1475 genes by transforming cre-lox system, and confirmed that these mutant strains had excellent producibility of phytoene, leading to the completion of the present invention.

SUMMARY OF THE INVENTION

It is an object of the present invention to provide a method for preparing a *Deinococcus* species mutant strain having deletion of DR0861 gene by using cre-lox system and a mutant strain prepared thereby.

It is another object of the present invention to provide a method for producing phytoene using the mutant strain above.

To achieve the above objects, the present invention provides a method for preparing a *Deinococcus* species mutant strain having deletion of DR0861 gene using cre-lox system, which comprises the steps of deleting DR0861 gene by introducing a DNA construct in which the upstream and downstream fragments of DR0861 gene were fused to both ends of the lox nucleic acid fragment containing a first selection marker in a *Deinococcus* species strain; deleting the first selection marker by introducing a vector comprising a groE promoter, a gene encoding cre recombinase, a second selection marker and a temperature sensitive repUts in the strain having deletion of DR0861 gene above; and eliminating the vector comprising the second selection marker by culturing the prepared mutant strain.

The present invention also provides a *Deinococcus* species mutant strain having deletion of DR0861 gene but having phytoene producibility which has been prepared by the method of the invention above.

The present invention also provides a method for producing phytoene comprising the step of culturing the mutant strain above.

Advantageous Effect

The *Deinococcus radiodurans* mutant strain prepared by the method of the present invention having high producibility of phytoene does not retain an artificial antibiotic-resistant gene, although constructed by introducing a metabolism engineering method, and has high producibility of phytoene. Thus, the mutant strain prepared according to the method can find useful applications in the mass production of phytoene.

DESCRIPTION OF THE PREFERRED EMBODIMENTS

Figure 1A:
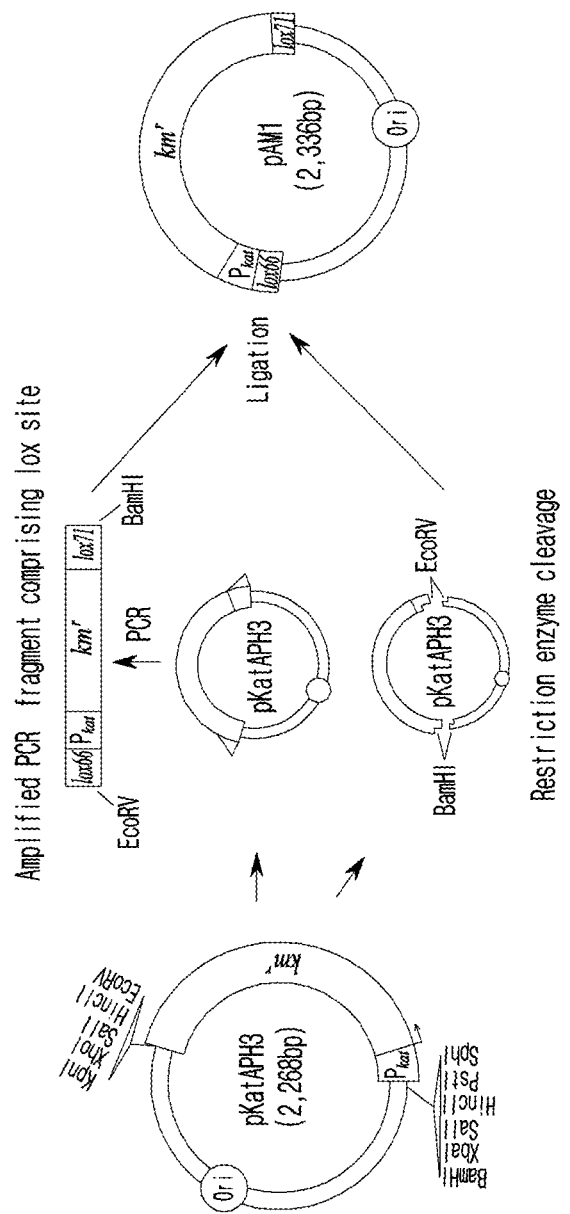
FIG. 1*a* is a diagram illustrating the preparation process of pAM1 plasmid.

Hereinafter, the present invention is described in detail.

The present invention provides a method for preparing a *Deinococcus* species mutant strain having deletion of DR0861 gene using cre-lox system, which comprises the steps of deleting DR0861 gene by introducing a DNA construct in which the upstream and downstream fragments of DR0861 gene were fused to both ends of the lox nucleic acid fragment containing a first selection marker in a *Deinococcus* species strain; deleting the first selection marker by introducing a vector comprising a groE promoter, a gene encoding cre recombinase, a second selection marker and a temperature sensitive repUts in the strain having deletion of DR0861 gene above; and eliminating the vector comprising the second selection marker by culturing the prepared mutant strain.

The term "cre-lox system" used in this invention indicates a site-specific recombinase technique used to perform deletions, insertions, translocations, and inversions at specific sites of DNA. The cre-lox system can be used to induce mutations in genes of eukaryotic and prokaryotic organisms. This system is composed of a cre recombination enzyme, a single enzyme, and is able to recombine the short target sequence lox sequence. A target gene can be activated or inhibited or replaced with another gene by arranging the lox sequence properly in a target site where a mutation is to be induced. In general, lox P is a bacteriophage P1 site consisting of 34 bases and has an asymmetric 8 bp base sequence, and has two pairs of palindromic structures in the size of 13 bp, except two bases in the center (ATAACTTCGTATA-NNNTANNN-TATACGAAGTTAT).

The term "selection marker" used in this invention indicates a specific gene product. A microorganism containing the said product displays a special trait that does not appear in microorganisms that do not contain the product, so that the microorganisms can be distinguished by that. The selection marker can be an antibiotic resistance gene. The antibiotic can be one or more antibiotics selected from the group consisting of kanamycin, chloramphenicol, spectinomycin and streptomycin, and particularly one or more antibiotics selected from the group consisting of kanamycin and chloramphenicol.

The *Deinococcus* species strain herein can be one or more strains selected from the group consisting of *D. radiodurans, D. indicus, D. caeni, D. aquaticus, D. depolymerans, D. grandis, D. daejeonensis, D. radiotolerans, D. geothermalis, D. ruber, D. antarcticus, D. proteolyticus, D. radiopugnans, D. radiophilus, D. cellulosilyticus* and *D. swuensis*, and particularly can be *Deinococcus radiodurans*.

The present invention provides the step of deleting DR0861 gene by introducing a DNA construct in which the upstream and downstream fragments of DR0861 gene were fused to both ends of the lox nucleic acid fragment containing a first selection marker in a *Deinococcus* species strain.

The term "DR0861" used in this invention indicates a gene encoding phytoene dehydrogenase playing a role in converting phytoene into zeta-carotene (ξ-carotene) by introducing double bonds at C11 and C11' sites of phytoene. The said phytoene dehydrogenase is also called phytoene desaturase. The DR0861 gene above can be a polynucleotide composed of any sequence known to those in the art. Particularly, the DR0861 gene above can be a polynucleotide composed of the nucleotide sequence represented by SEQ. ID. NO: 22.

The upstream and downstream fragments of the DR0861 gene can be 0.5-1.2 kb, particularly 0.6-1.1 kb and more particularly 0.7-1.0 kb long sequence from 5' or 3' end of the full length DR0861 gene. The fragments above can be included for homologous recombination with DR0861 gene present in the *Deinococcus* species strain genome.

The term "lox nucleic acid fragment" used in this invention indicates a fragment for removing a target gene from the *Deinococcus* species strain genome using the cre-lox system. According to an embodiment of the present invention, the lox nucleic acid fragment can include a first selection marker having lox fragments at both ends. The lox nucleic acid fragment can include one or more lox genes selected from the group consisting of lox71 and lox66 at both ends of the fragment. Particularly, the lox nucleic acid fragment can be a polynucleotide composed of the nucleotide sequence represented by SEQ. ID. NO: 17.

The present invention also provides the step of deleting the first selection marker by introducing a vector comprising a groE promoter, a gene encoding cre recombinase, a second selection marker and a temperature sensitive repUts in the strain having deletion of DR0861 gene above.

The groE promoter can be operably linked to cre recombinase. The term "operably linked" herein indicates that a sequence regulating the expression of nucleic acid is linked to a nucleic acid sequence encoding a target protein to be operated. In the preparation of a recombinant vector, the operably linking can be performed by the conventional methods well known to those in the art. The groE promoter above can be a polynucleotide comprising 299 bp of the upstream region of greES gene (NCBI GeneBank ID: 1800077), particularly, a polynucleotide composed of the nucleotide sequence represented by SEQ. ID. NO: 18.

On the other hand, the second selection marker can be operably linked to Kat promoter. At this time, the Kat promoter can be a polynucleotide comprising 138 bp of the upstream region of KatE1 gene (NCBI GeneBank ID: 1800077), particularly, a polynucleotide composed of the nucleotide sequence represented by SEQ. ID. NO: 19.

The term "temperature sensitive repUts" used in this invention indicates repU gene, a gene that makes plasmid replication possible only in a certain temperature range (H. H. Nguyen et al., *Molecular Microbiology*, 2009, 73(2), 240-252). A plasmid containing the gene above can be replicated at 28° C. so as to maintain in a host cell. However, at the temperature of 37° C., the plasmid is not replicated and therefore it is removed from the host cell. The repU gene and the plasmid containing the gene are well known to those in the art.

The step of deleting the first selection marker is as follows. Lox genes coupled to both ends of the first selection marker are recognized and cleaved by the cre recombinase, and accordingly the first selection marker is eliminated from the *Deinococcus* species strain genome.

In the step above, the vector comprising a groE promoter, a gene encoding cre recombinase, a second selection marker and a temperature sensitive repUts can be a polynucleotide composed of the nucleotide sequence represented by SEQ. ID. NO: 21.

The present invention also provides the step of eliminating the vector comprising the second selection marker by culturing the mutant strain obtained above.

The second selection marker can be eliminated using a property that the vector including the second selection marker is not replicated within a certain temperature range by the temperature sensitive marker repUts. Thus, in this step, the vector comprising the second selection marker can be eliminated by culturing the mutant strain for a certain period of time within a certain temperature range. Particularly, the temperature for the culture can be 30-40° C., preferably 31-39° C. and more preferably 33-38° C.

The mutant strain obtained according to the above step can be selected based on the characteristics that the strain is not grown in the medium containing antibiotics after the elimination of the first and the second selection markers.

The present invention can further include the step of introducing a plasmid respectively expressing one or more genes selected from the group consisting of DR0862, DR1087, DR1395 and DR1475.

The term "DR0862" used in this invention indicates a gene encoding phytoene synthase. The phytoene synthase can synthesize phytoene by using the precursor geranylgeranyl pyrophosphate as a substrate. The said DR0862 gene can be a polynucleotide composed of any sequence well known to those in the art. Particularly, the DR0862 gene can be a polynucleotide composed of the nucleotide sequence represented by SEQ. ID. NO: 41.

The term "DR1087" used in this invention indicates a gene encoding isopentenyl pyrophosphate isomerase. The isopentenyl pyrophosphate isomerase can isomerize isopentenyl pyrophosphate to dimethylallyl pyrophosphate. The said DR1087 gene can be a polynucleotide composed of any sequence well known to those in the art. Particularly, the DR1087 gene can be a polynucleotide composed of the nucleotide sequence represented by SEQ. ID. NO: 42.

The term "DR1395" used in this invention indicates a gene encoding geranylgeranyl pyrophosphate synthase. The geranylgeranyl pyrophosphate synthase can synthesize geranylgeranyl pyrophosphate by using fanesyl pyrophosphate as a substrate. The said DR1395 gene can be a polynucleotide composed of any sequence well known to those in the art. Particularly, the DR1395 gene can be a polynucleotide composed of the nucleotide sequence represented by SEQ. ID. NO: 43.

The term "DR1475" used in this invention indicates a gene encoding 1-deoxy-D-xylulose-5-phosphate synthase. The 1-deoxy-D-xylulose-5-phosphate synthase can synthesize 1-deoxy-D-xylulose-5-phosphate by using pyruvate and glucose-3-phosphate as substrates. The said DR1475 gene can be a polynucleotide composed of any sequence well known to those in the art. Particularly, the DR1475 gene can be a polynucleotide composed of the nucleotide sequence represented by SEQ. ID. NO: 44.

Particularly, the method of the present invention can additionally include the step of introducing a plasmid expressing one, two or more genes selected from the group consisting of DR0862, DR1087 and DR1475. At this time, the introduction can be performed by using the plasmid constructed to express one, two or more genes above or one, two or more plasmids constructed to express each of the genes above respectively. The method for engineering to overexpress one, two or more genes in a strain is well known to those in the art.

The plasmid expressing one or more genes selected from the group consisting of DR0862, DR1087 and DR1475 can be constructed by the conventional method well known to those in the art. The method to introduce the plasmid in a strain can also be performed by those in the art.

The present invention can further include the step of deleting DR2250 gene.

The term "DR2250" used in this invention indicates a gene encoding methoxyneurosporene dehydrogenase, the carotenoid 3', 4' desaturase. The methoxyneurosporene dehydrogenase can introduce a double bond into C3' and C4' sites of carotenoid. The said DR2250 gene can be a polynucleotide composed of any sequence well known to those in the art. Particularly, the DR2250 gene can be a polynucleotide composed of the nucleotide sequence represented by SEQ. ID. NO: 45.

The method for deleting the DR2250 gene can be performed by any method well known to those in the art. As an example, the deletion of DR2250 gene can be performed by the same manner as the method used for the deletion of DR0861 gene described above.

The polynucleotide of the present invention can include variants or fragments having different sequences by deletion, insertion, substitution or addition of nucleotides within a range that does not affect the function of the encoding protein. The gene can have at least 70%, 80%, 90%, 95% or 99% homology with a polynucleotide consisting of the informed nucleotide sequence.

In a preferred embodiment of the present invention, the present inventors constructed a plasmid comprising lox fragments at both ends and including chloramphenicol as the first selection marker (see FIG. 1a). The present inventors also constructed a plasmid comprising the second selection marker regulating the cre gene expression by groE promoter and including temperature sensitive repUts (see FIG. 1b).

Figure 4:
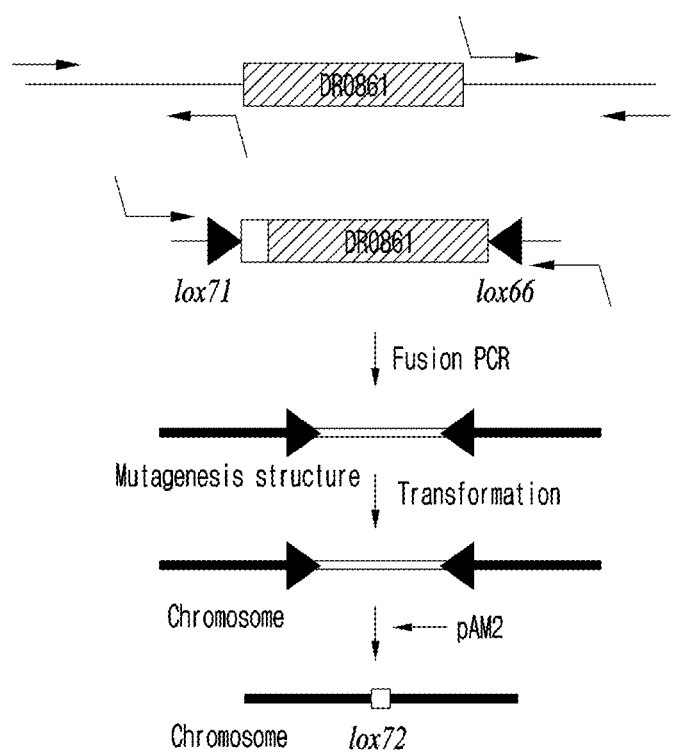
FIG. 4 is a diagram illustrating the deletion process of DR0861 gene from a *Deinococcus radiodurans* strain genome.

The upstream and downstream fragments of the target gene DR0861 were fused to the DNA construct including the first selection marker, which was introduced into a Deinococcus radiodurans strain to select a mutant strain having deletion of DR0861 gene (see FIG. 4). To eliminate the first selection marker from the selected strain, a vector containing the second selection marker expressing cre recombinase was introduced therein, leading to the selection of a mutant strain with the elimination of the first selection marker. To eliminate the second selection marker from the strain above with the elimination of the first selection marker, the strain was cultured at 37° C. and then those strains that grew only in the antibiotics-free medium were selected. As a result, after the elimination of all the selection markers, a Deinococcus radiodurans strain having deletion of DR0861 gene was selected (see FIG. 6).

Figure 9:
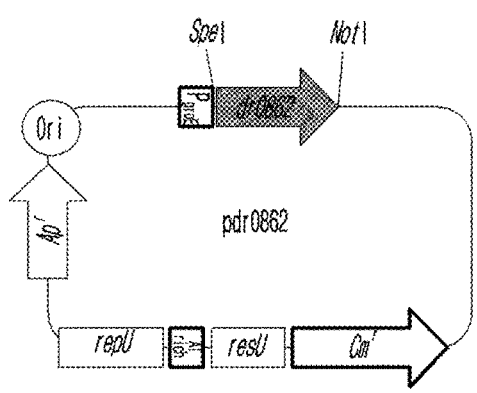
FIG. 9 is a diagram illustrating the structure of the plasmid expressing DR0862 gene.
Figure 10:
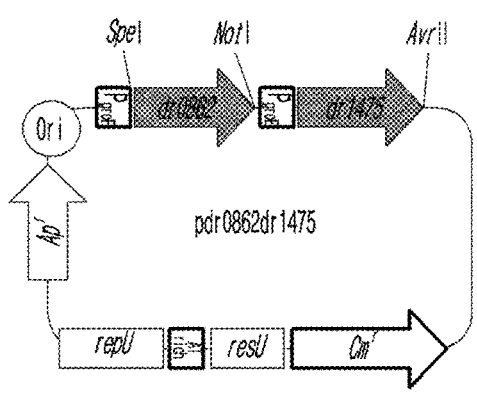
FIG. 10 is a diagram illustrating the structure of the plasmid expressing DR0862 and DR1475 genes at the same time.

The present inventors constructed Deinococcus mutant strains having deletion of DR0861 gene and at the same time overexpressing DR0862, DR1087, DR1395, DR1475, DR0862 and DR1087, DR0862 and DR1395, or DR0862 and DR1475 genes by introducing the plasmid expressing DR0862, DR1087, DR1395, DR1475, DR0862 and DR1087, DR0862 and DR1395, or DR0862 and DR1475 genes into the Deinococcus radiodurans strain having deletion of DR0861 gene (see FIGS. 9 and 10). Further, the present inventors constructed Deinococcus mutant strains having deletion of DR0861 and DR2250 genes and at the same time overexpressing DR0862 and DR1475 genes.

The present invention also provides a Deinococcus species mutant strain having deletion of DR0861 gene but having phytoene producibility which has been prepared by the method of the invention above.

The Deinococcus species mutant strain can be prepared according to the method described above. Particularly, the Deinococcus species strain herein can be one or more strains selected from the group consisting of D. radiodurans, D. indicus, D. caeni, D. aquaticus, D. depolymerans, D. grandis, D. daejeonensis, D. radiotolerans, D. geothermalis, D. ruber, D. antarcticus, D. proteolyticus, D. radiopugnans, D. radiophilus, D. cellulosilyticus and D. swuensis, and specifically can be Deinococcus radiodurans The Deinococcus species mutant strain having deletion of DR0861 gene can have excellent phytoene producibility.

Figure 7A:
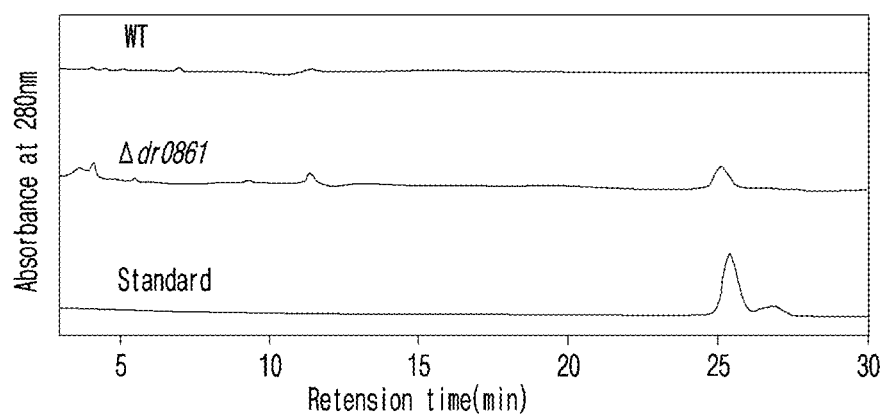
FIG. 7a is a graph illustrating the phytoene producibility of the *Deinococcus radiodurans* mutant strain having deletion of DR0861 gene prepared according to the method of the present invention, confirmed by HPLC.
Figure 7B:
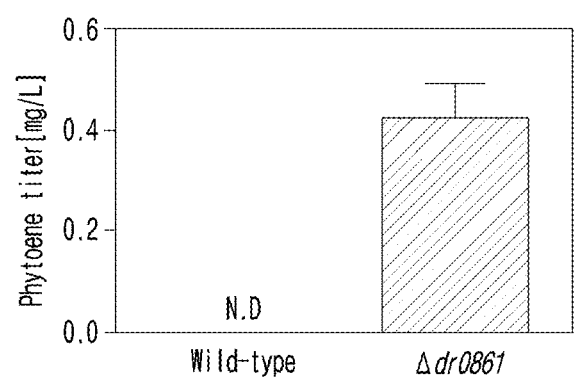
FIG. 7b is a graph illustrating the comparison of the phytoene producibility between the *Deinococcus radiodurans* mutant strain having deletion of DR0861 gene prepared according to the method of the present invention and the wild type strain.
Figure 8:
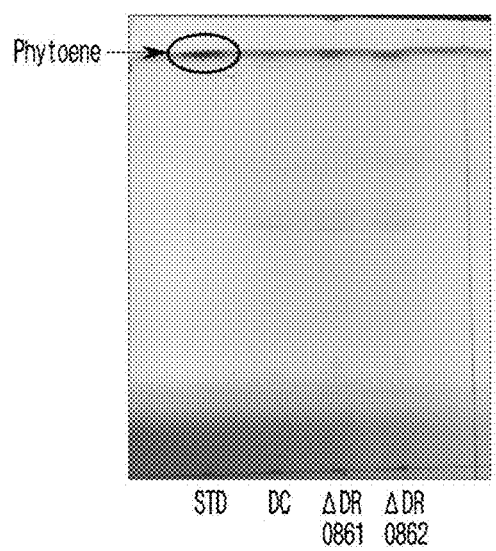
FIG. 8 is a set of photographs illustrating the phytoene producibility of the *Deinococcus radiodurans* mutant strain having deletion of DR0861 gene prepared according to the method of the present invention, confirmed by TLC (STD: standard phytoene; DC: wild type *Deinococcus radiodurans*; ΔDR0861: *Deinococcus radiodurans* mutant strain having deletion of DR0861 gene; ΔDR0862: *Deinococcus radiodurans* mutant strain having deletion of DR0862 gene).

In a preferred embodiment of the present invention, the inventors confirmed through HPLC and TLC that the Deinococcus species strain having deletion of DR0861 gene prepared by the method of the present invention had excellent phytoene producibility (see FIGS. 7 and 8).

Figure 13:
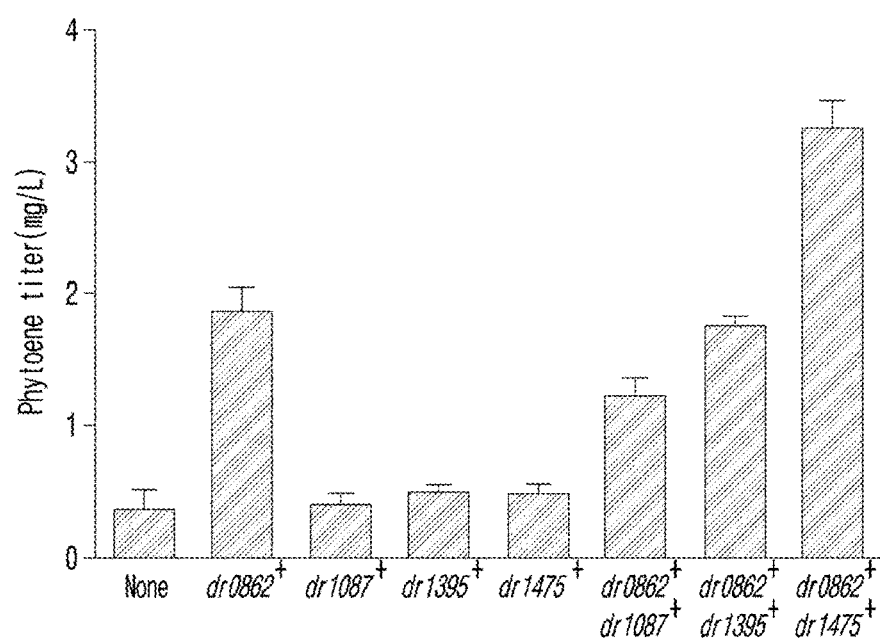
FIG. 13 is a graph illustrating the quantification of the phytoene producibility of the mutant strains prepared in Examples 6-13, measured by HPLC (None: Example 6; dr0862$^+$: Example 7; dr1087$^+$: Example 8; dr1395$^+$: Example 9; dr1475$^+$: Example 10; dr0862$^+$, dr1087$^+$: Example 11; dr0862$^+$, dr1395$^+$: Example 12; dr0862$^+$, dr1475$^+$: Example 13).

The present inventors also confirmed that the Deinococcus mutant strains having deletion of DR0861 gene and at the same time overexpressing DR0862, DR1087, DR1395, DR1475, DR0862 and DR1087, DR0862 and DR1395, or DR0862 and DR1475 genes had excellent phytoene producibility, and particularly the Deinococcus mutant strains having deletion of DR0861 gene and overexpressing DR0862 and DR1475 genes displayed the most excellent phytoene producibility (see FIG. 13). The mutant strain having deletion of DR0861 gene and overexpressing DR0862 and DR1475 genes displayed the highest phytoene producibility 72 hours after the culture (see FIG. 14). Further, the present inventors constructed mutant strains having deletion of DR0861 and DR2250 genes and overexpressing DR0862 and DR1475 genes, from which the inventors confirmed that these strains had more excellent phytoene producibility than those mutant strains having deletion of DR0861 gene and overexpressing DR0862 and DR1475 genes (see FIG. 15). In addition, the mutant strain having deletion of DR0861 and DR2250 genes and overexpressing DR0862 and DR1475 genes displayed the highest phytoene producibility 72 hours after the culture (see FIG. 16).

The present invention also provides a method for producing phytoene comprising the step of culturing the mutant strain prepared according to the present invention having the characteristics described above.

The culture can be performed in a proper medium and culture conditions well known to those in the art. Particularly, the culture can be batch culture, continuous culture or fed-batch culture. The method for producing phytoene can further comprise the step of obtaining phytoene from the culture product obtained by culturing the mutant strain. Obtaining phytoene can be properly performed by a person skilled in the art.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Construction of Plasmid Comprising the First Selection Maker

A plasmid containing lox66 and lox71 genes at both ends of the kanamycin resistance gene was constructed as follows (FIG. 1a).

First, the kanamycin resistance gene was amplified to have lox66 and lox71 genes at both ends using pKatAPH3 plasmid (Satoh K. et al., Microbiology, 152:3217-3226, 2006) with the Lox66F (SEQ. ID. NO: 1) and Lox71R (SEQ. ID. NO: 2) primers having the nucleotide sequences listed in Table 1 below. Particularly, 1 $\mu\ell$ of pKatAPH3, 1 $\mu\ell$ of each lox66F and lox71R primers (10 pmole/$\mu\ell$) and 17 $\mu\ell$ of sterile distilled water were all mixed, and then the mixture was added to pfu polymerase mix (Bioneer), followed by amplification using T-100 Thermal cycler DNA amplifier (Bio-rad). PCR was performed as follows: reacting at 95° C. for 5 minutes, and 30 cycles of reacting at 95° C. for 30 seconds, at 60° C. for 30 seconds and at 72° C. for 1 minute.

TABLE 1

| SEQ. ID. NO: | Name | Sequence (5'→3') |
|---|---|---|
| SEQ. ID. NO: 1 | Lox66F | gcttgatatctaccgttcgtatagcatacatt atacgaagttat |
| SEQ. ID. NO: 2 | Lox71R | tagaggatcctaccgttcgtataatgtatgct atacgaagttat |
| SEQ. ID. NO: 3 | GroEF | cgtggcggccgctcggcttggaagcacgtatt |
| SEQ. ID. NO: 4 | GroER | tacgggcagtaaattggacatatccactagta acggccgcc |
| SEQ. ID. NO: 5 | CreF | ggcggccgttactagtggatatgtccaattta ctgcccgta |
| SEQ. ID. NO: 6 | CreR | agcttatcgataccgtcgacctaatcgccatc ttccagca |
| SEQ. ID. NO: 7 | pKatF | tgctggaagatggcgattaggtcgacggtatc gataagct |
| SEQ. ID. NO: 8 | pKatR | ccagtgatttttttctccatatgctctccttc gcctcgct |
| SEQ. ID. NO: 9 | CmF | agcgaggcgaaggagagcatatggagaaaaaa atcactgg |
| SEQ. ID. NO: 10 | CmR | gcgactcgaggtcgactctagaggatcctc |

Figure 2:
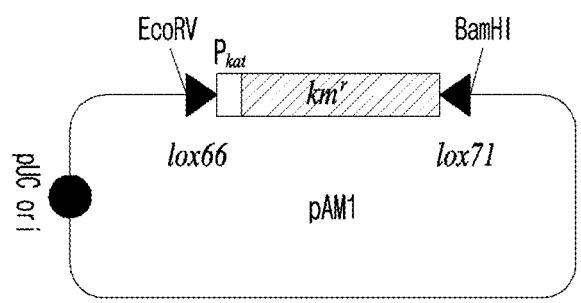
FIG. 2 is a diagram illustrating the structure of the prepared pAM1 plasmid.

The obtained product was confirmed by electrophoresis on 1% agarose gel, which was purified using a DNA fragment purification kit (Intron lifetechnology). The obtained PCR product and pKatAPH3 were digested with EcoRV and BamHI, respectively, and ligated to construct a plasmid containing lox66 and lox71 genes at both ends of the kanamycin resistance gene. The constructed plasmid was named pAM1 (SEQ. ID. NO: 20) (FIG. 2).

Figure 1B:
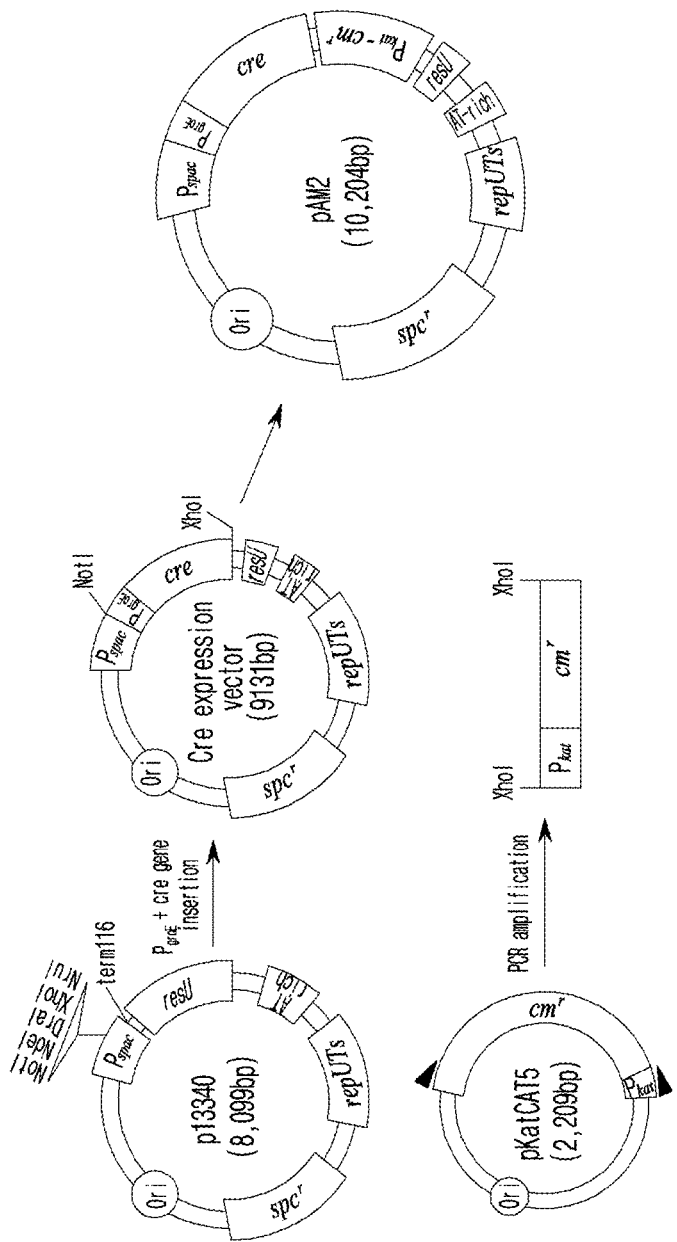
FIG. 1b is a diagram illustrating the preparation process of pAM2 plasmid.

Example 2: Construction of Plasmid Comprising the Second Selection Marker in which Cre Gene Expression is Regulated by groE Promoter A plasmid comprising a chloramphenicol resistant gene and a groE promoter was constructed by the following method (FIG. 1b).

<2-1> Obtainment of groE Promoter Gene

To obtain a groE promoter gene, PCR was performed by the same manner as described in Example 1 except that the *Deinococcus radiodurans* gene was used as a template and 0.5 μℓ of each GroEF (SEQ. ID. NO: 3) and GroER (SEQ. ID. NO: 4) primers listed in Table 1 above and AccuPower™ pfu PCR premix mix (Bioneer) were used. As a result, a PCR product of the groE promoter gene was obtained.

<2-2> Obtainment of cre Gene

To obtain a cre gene, PCR was performed by the same manner as described in Example 1 except that the artificially synthesized polynucleotide (Bioneer) was used as a template and the CreF (SEQ. ID. NO: 5) and CreR (SEQ. ID. NO: 6) primers listed in Table 1 above were used. As a result, a PCR product of the cre gene was obtained.

<2-3> Linking groE Promoter Gene and cre Gene

PCR was performed by the same manner as described in Example 1 except that a mixture of the PCR products obtained in Examples <2-1> and <2-2> was used as a template and the GroEF (SEQ. ID. NO: 3) and CreR (SEQ. ID. NO: 6) primers listed in Table 1 were used. As a result, a PCR product in the form of a fusion of the groE promoter gene and the cre gene was obtained.

<2-4> Obtainment of KatE1 Promoter

PCR was performed by the same manner as described in Example 1 except that the *Deinococcus radiodurans* gene was used as a template and the pKatF (SEQ. ID. NO: 7) and pKatR (SEQ. ID. NO: 8) primers listed in Table 1 were used. As a result, a PCR product of the KatE1 gene was obtained.

<2-5> Obtainment of Chloramphenicol Resistant Gene

To obtain a chloramphenicol resistant gene, PCR was performed by the same manner as described in Example 1 except that pRAD1 plasmid (Meima R. et at., Applied and environmental microbiology 66:3856-3867, 2000) was used as a template and the CmF (SEQ. ID. NO: 9) and CmR (SEQ. ID. NO: 10) primers listed in Table 1 above were used. As a result, a PCR product of the chloramphenicol resistant gene was obtained.

<2-6> Linking KatE1 Promoter Gene and Chloramphenicol Resistant Gene

PCR was performed by the same manner as described in Example 1 except that a mixture of the PCR products obtained in Examples <2-4> and <2-5> was used as a template and the pKatF (SEQ. ID. NO: 7) and CmR (SEQ. ID. NO: 10) primers listed in Table 1 were used. As a result, a PCR product of the chloramphenicol resistant gene was obtained.

<2-7> Linking groE Promoter Gene, cre Gene, KatE1 Promoter Gene and Chloramphenicol Resistant Gene PCR was performed by the same manner as described in Example 2 except that a mixture of the PCR products obtained in Examples <2-3> and <2-6> was used as a template and the GroEF (SEQ. ID. NO: 3) and CmR (SEQ. ID. NO: 10) primers listed in Table 1 were used. As a result, a PCR product in the form of a fusion of the groE promoter gene, the cre gene, the KatE1 promoter gene and the chloramphenicol resistant gene was obtained.

<2-8> Construction of Plasmid Comprising the Second Selection Marker

Figure 3:
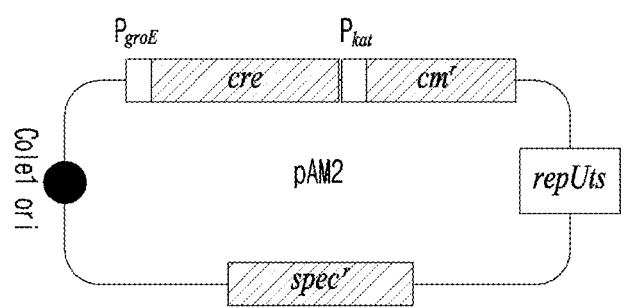
FIG. 3 is a diagram illustrating the structure of the prepared pAM2 plasmid.

The PCR product obtained in Example<2-7> and 13840 plasmid (Nguyen, H. H. et al., *Molecular microbiology*, 73:240-252, 2009) were digested with NotI and XhoI (Enzynomics), and ligated to construct a plasmid. The constructed plasmid was named pAM2 (SEQ. ID. NO: 21) (FIG. 3).

Comparative Example 1: Construction of Plasmid Comprising the Second Selection Marker in which cre Gene Expression is Regulated by KatE1 Promoter A plasmid comprising the second selection marker in which the cre gene expression is regulated by KatE1 promoter was constructed by the same manner as described in Example 2 except that the KatE1 promoter was introduced in the groE promoter site.

Example 3. Preparation of *Deinococcus Radiodurans* Mutant Strain Having Deletion of DR0861 Gene <3-1> Obtainment of Upstream and Downstream Regions of DR0861 Gene PCR was performed by the same manner as described in Example 1 except that the *Deinococcus radiodurans* DNA was used as a template and the primers 1, 2, 5 and 6 (SEQ. ID. NO: 11, NO: 12, NO: 15 and NO: 16) listed in Table 2 below were used for the amplification of the upstream (1 kb) and downstream (1 kb) regions of DR0861 gene. As a result, PCR products of the upstream (1 kb) and downstream (1 kb) regions of DR0861 gene were obtained, respectively.

TABLE 2

| SEQ. ID. NO: | Name | Sequence (5'→3') |
|---|---|---|
| SEQ. ID. NO: 11 | Primer 1 | catagtgaaagaaacgtctg |
| SEQ. ID. NO: 12 | Primer 2 | agcttatcgataccgtcgacgacagtaaacc tcggaagtc |
| SEQ. ID. NO: 13 | Primer 3 | gacttccgaggtttactgtcgtcgacggtat cgataagct |
| SEQ. ID. NO: 14 | Primer 4 | ttaagcggaatccgtatgaccatgcctgcag gtcgactct |
| SEQ. ID. NO: 15 | Primer 5 | agagtcgacctgcaggcatggtcatacggat tccgcttaa |
| SEQ. ID. NO: 16 | Primer 6 | ttggtccacatgctggtgca |

<3-2> Amplification of Kanamycin Resistant Gene Containing Lox Genes on Both Sides PCR was performed by the same manner as described in Example 1 except that the pAM1 plasmid constructed in Example 1 was used as a template and the primers 3 and 4 (SEQ. ID. NO: 13 and NO: 14) listed in Table 2 were used for the amplification of the kanamycin resistant gene containing lox71 and lox66 genes on both sides. As a result, a PCR product of the kanamycin resistant gene containing lox71 and lox66 genes on both sides was obtained.

<3-3> Linking Upstream and Downstream Regions of DR0861 Gene and Kanamycin Resistant Gene Containing Lox Genes on Both Sides First, the PCR products obtained in Examples <3-1> and <3-2> were electrophoresed on 1% agarose gel, followed by purification using DNA fragment purification kit (Intron lifetechnology). The purified PCR products were mixed, which was used as a template. PCR was performed by the same manner as described in Example 1 except that the primers 1 (SEQ. ID. NO: 11) and 6 (SEQ. ID. NO: 16) listed in Table 2 were used and the reaction at 72° C. was induced for 3 minutes. As a result, a PCR product in the form of a fusion of the upstream and downstream regions of DR0861 gene and the kanamycin resistant gene containing lox genes on both sides was obtained (FIG. 4).

<3-4> Construction of Mutant Strain Having Deletion of DR0861 Gene

First, a *Deinococcus radiodurans* strain (ATCC 13939, The RDA-Genebank Information Center, Korea) was cultured in TGY medium (0.5% (w/v) trypton, 0.1% (w/v) glucose and 0.3% (w/v) yeast extract) at 30° C. until $OD_{600}$ reached 0.5. The cultured cells were centrifuged and suspended in 2× TGY medium containing 30 mM calcium chloride ($CaCl_2$). The suspension was allowed to stand on ice for 1 hour. The suspension was centrifuged again to remove the supernatant. 50 µℓ of TGY medium containing 30 mM $CaCl_2$ and 10% (v/v) glycerol was added thereto, followed by resuspension. The prepared solution was distributed in 1.5 mℓ a tubes (50 µℓ /tube).

On the other hand, the PCR product obtained in Example <3-3> was electrophoresed on 1% agarose gel, followed by purification using DNA fragment purification kit (Intron lifetechnology). 10 µℓ of the purified PCR product was mixed with 50 µℓ of 2× TGY medium containing *Deinococcus radiodurans* cells and 30 mM $CaCl_2$ at 50° C. The mixture was allowed to stand on ice for 30 minutes, followed by reaction at 32° C. for 1.5 hours. Upon completion of the reaction, 900 µℓ of 2× TGY medium was added thereto, followed by culture at 30° C. for 12 hours. The cultured strain (200 µℓ) was plated on 2× TGY solid medium containing 25 µg/mℓ of kanamycin, followed by culture at 30° C. for 3 to 4 days. DNA was extracted from the cultured strain, followed by sequencing to confirm whether DR0861 gene was deleted. The final selected strain was named DrAM1.

Example 4: Elimination of Antibiotic Resistant Gene from the Mutant Strain Having Deletion of DR0861 Gene First, the mutant strain having deletion of DR0861 gene prepared in Example 3 was transformed with the pAM2 plasmid constructed in Example 2 by the same manner as described in Example <3-4>. To select a kanamycin resistant gene deficient strain from the transformed strain, the strain was plated on 2× TGY solid medium containing 3 µg/mℓ of chloramphenicol, followed by culture. DNA was extracted from the cultured strain, followed by sequencing to confirm whether the kanamycin resistant gene was deleted. The final selected strain was named DrAM2.

Example 5: Confirmation of Expression of cre Protein by groE or KatE1 Promoter The expression levels of cre protein in the mutant strain introduced with the plasmid containing the second selection marker in which the cre protein expression is regulated by the groE promoter and in the mutant strain introduced with the plasmid containing the second selection marker in which the cre protein expression is regulated by the KatE1 promoter constructed in Example 3 was measured by the following method.

Particularly, a *Deinococcus radiodurans* strain transfected with a plasmid containing groE promoter or KatE1 promoter was cultured in TGY medium until OD reached 1.

Only those cells containing each promoter were obtained from the culture medium by centrifugation, to which lysis buffer was added. The cells were lysed using an ultrasonicator. Each cell lysate was centrifuged at 4,000 rpm, 4° C. for 20 minutes to recover the supernatant containing protein. The protein included in each supernatant was quantified by Bradford assay. 10 µg of the quantified protein was electrophoresed on SDS-PAGE gel, followed by staining with coomassie blue. Then, the changes of a band corresponding to the cre protein size of about 35 kDa were observed.

Figure 5:
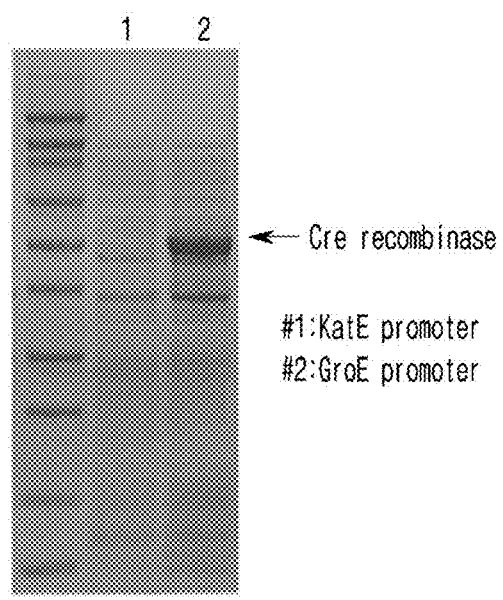
FIG. 5 is a set of photographs illustrating the expression levels of the cre recombinase according to the plasmid for controlling the cre gene expression.

As a result, as shown in FIG. 5, the expression amount of cre protein in the mutant strain introduced with the plasmid containing the second selection marker in which the cre protein expression is regulated by the groE promoter was higher than that in the mutant strain introduced with the plasmid containing the second selection marker in which the cre protein expression is regulated by the KatE1 promoter (FIG. 5).

Example 6: Construction of *Deinococcus Radiodurans* Strains Having Deletion of Both Antibiotic Resistance Gene and DR0861 Gene The pAM2 plasmid constructed in Example 2 is a temperature sensitive plasmid, which is not replicated in *Deinococcus radiodurans* strains at 37° C. Based on that, the pAM2 plasmid was removed from DrAM2 strain by the following method.

Figure 6:
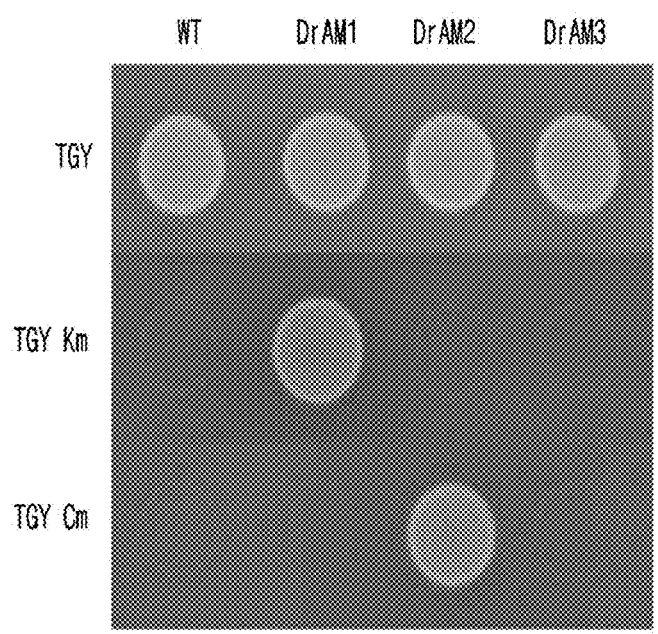
FIG. 6 is a set of photographs illustrating the selected *Deinococcus radiodurans* mutant strain having deletion of DR0861 gene and deletion of all antibiotic-resistant genes.

Particularly, DrAM2 strain was cultured in TGY liquid medium at 37° C. for 24 hours. The cultured DrAM2 strain was diluted at the volume ratio of 1:10,000, which was plated on 2× TGY solid medium, followed by further culture at 30° C. for 2 days. The formed single colony was inoculated on 2× TGY solid medium containing kanamycin or chloramphenicol using a sterilized tip or on antibiotics-free 2× TGY solid medium, followed by culture at 30° C. for 1 day. Upon completion of the culture, a single colony growing on antibiotics-free medium only was selected and named DrAM3 (FIG. 6).

Comparative Example 2: Construction of *Deinococcus Radiodurans* Strain Having Deletion of DR0862 Gene A *Deinococcus radiodurans* mutant strain having deletion of DR0862 gene was constructed by the same manner as described above except that DR0862 gene was deleted instead of DR0861 gene.

Experimental Example 1: Confirmation of Phytoene Producibility of *Deinococcus Radiodurans* Mutant Strain Having Deletion of DR0861 Gene <1-1> Culture of Strain and Obtainment of Culture Product First, 10 g of trypton (BD, France), 10 g of yeast extract (Acumedia, USA), 2 g of glucose (Duksan, Korea) and 2 g of $K_2HPO_4$ (Daejung, Korea) were dissolved in 1 ℓ of purified water and the pH was adjusted to 6.5 to prepare a liquid medium. The prepared liquid medium was distributed in three 500 mℓ Erlenmeyer flasks (100 mℓ/flask), which were autoclaved. 1 mℓ of the mutant strain prepared in Example 6, the mutant strain prepared in Comparative Example 2, or a wild type *Deinococcus radiodurans* strain was inoculated in the sterilized liquid medium. The strain was cultured at 30° C., 200 rpm for 72 hours with stirring. Upon completion of the culture, the culture solution was centrifuged at 4° C., 4,000 rpm to recover the pulverized cells. 1 mℓ of ethyl acetate was added to the recovered cells, followed by stirring for 15 minutes. The obtained suspension was filtered under reduced pressure using a filter paper with a pore size of 0.45 µm and evaporated to give the culture residue.

<1-2> Confirmation of Phytoene Producibility Through High Performance Liquid Chromatography (HPLC)

The phytoene producibility was analyzed by HPLC using the residues obtained from the *Deinococcus radiodurans* strain having deletion of DR0861 gene and the wild type *Deinococcus radiodurans* strain obtained in Experimental Example <1-1>.

Particularly, Zorbax Eclipse XDB-C18 5 µm (4.6×250 mm) was used as the HPLC column, the temperature was set at 35° C. and the flow rate was 2.0 mℓ/min. On the other hand, the residue prepared in Experimental Example <1-1> was injected at the volume 5 µl. As a moving phase, a mixture of acetonitrile, methanol and isopropanol (40:50:10) was used. At this time, 15-cis-phytoene (>95%, Toronto Research Chemical) was used as a standard for comparison.

As a result, as shown in FIG. 7*a*, it was confirmed that the wild type strain did not produce phytoene, but the strain having deletion of DR0861 gene demonstrated excellent phytoene producibility (FIG. 7*a*). As a result of confirming the amount of phytoene production, as shown in FIG. 7*b*, approximately at least 0.4 mg/ℓ of phytoene was produced in the strain having deletion of DR0861 gene (FIG. 7*b*).

<1-3> Confirmation of Phytoene Producibility Through Thin Layer Chromatography (TLC)

First, a silica gel plate (TLC silica gel 60, MERCK) for TLC was prepared in the size of 5×6.5 cm. The culture residue obtained in Experimental Example <1-1> was plated on the baseline positioned on the stationary phase of the prepared plate. At this time, the baseline was positioned about 1 to 3 cm away from the bottom of the plate, and the sample was applied in the form of spots. A mixture comprising fluoroform:methanol:acetone:acetic acid at the volume ratio of 10:1:0.4:0.2 was used as a developing solvent, which was added to a developing chamber as much as up to 1 cm from the bottom. The TLC plate loaded with the sample was fixed in the developing chamber with the bottom of the plate touching the developing solvent but with the baseline not touching the developing solvent. Then, the developing chamber was covered with a lid to seal the chamber. The development was completed when the development solvent was spread up to 1 cm away from the top of the plate. The developing solvent was evaporated from the plate after the development was completed. 10% sulfuric acid was applied to the plate, and the plate was placed on a hot plate at 120° C., followed by heating until the sample was separated.

As a result, as shown in FIG. 8, it was confirmed that the mutant strain having deletion of DR0861 gene demonstrated excellent phytoene producibility (FIG. 8).

Example 7: Construction of *Deinococcus Radiodurans* Mutant Strain Having Deletion of DR0861 Gene and Overexpressing DR0862 Gene A *Deinococcus radiodurans* mutant strain having deletion of DR0861 gene and overexpressing DR0862 gene was constructed by transfecting the DR07861 gene deficient

*Deinococcus radiodurans* strain with a plasmid overexpressing DR0862 (crtB) gene known as a rate-limiting enzyme.

First, PCR was performed to obtain DR0862 gene by the same manner as described in Example 1 except that the *Deinococcus radiodurans* gene was used as a template and the dr0862F1 (SEQ. ID. NO: 23) and dr0862R1 (SEQ. ID. NO: 24) primers listed in Table 3 below, 0.5 µℓ each, and AccuPower™ pfu PCR premix mix (Bioneer) were used.

TABLE 3

| SEQ. ID. NO: | Name | Sequence (5'→3') |
|---|---|---|
| SEQ. ID. NO: 23 | dr0862F1 | aagtactagtatgaggtctagggccggtt |
| SEQ. ID. NO: 24 | dr0862R1 | ctatgcggccgctcagccgtggaccgcgcca |
| SEQ. ID. NO: 25 | dr1087F1 | gttaactagtatgcggctggacactgtgtt |
| SEQ. ID. NO: 26 | dr1087R1 | ctaggcggccgcccttgcagagggggtcccttta |
| SEQ. ID. NO: 27 | dr1395F1 | aagtactagtatgcgtcccgaactgctcgc |
| SEQ. ID. NO: 28 | dr1395R1 | ataggcggccgctcacttctcccgcgtcgcca |
| SEQ. ID. NO: 29 | dr1475F1 | ctagactagtgtgaacgaacttcccggcac |
| SEQ. ID. NO: 30 | dr1475R1 | taacgcggccgcctacacctcaatcggcacgt |

The obtained PCR product was electrophoresed on 1% agarose gel, followed by purification using a DNA fragment purification kit (Intron lifetechnology). The purified PCR product and pRADZ3 plasmid (Meima R. and Lidstrom M. E., Applied environmental microbiology, 66:3856-3867) were digested with SpeI and NotI, and then ligated to construct a plasmid to express DR0862 gene at the downstream of the groE promoter in pRADZ3 (FIG. 9). The DR0862 deficient strain prepared in Example 6 was transfected with the prepared plasmid by the same manner as described in Example <3-4>. As a result, a *Deinococcus radiodurans* mutant strain having deletion of DR0861 gene and overexpressing DR0862 gene was constructed.

Example 8: Construction of *Deinococcus Radiodurans* Mutant Strain Having Deletion of DR0861 Gene and Overexpressing DR1087 Gene A *Deinococcus radiodurans* mutant strain having deletion of DR0861 gene and overexpressing DR1087 gene was constructed by transfecting the DR07861 gene deficient *Deinococcus radiodurans* strain with a plasmid overexpressing DR1087 (idi) gene known as a rate-limiting enzyme. The experiment was performed by the same manner as described in Example 7 except that the dr1087F1 (SEQ. ID. NO: 25) and dr1087R1 (SEQ. ID. NO: 26) primers listed in Table 3 were used to obtain DR1087 gene. As a result, a *Deinococcus radiodurans* mutant strain having deletion of DR0861 gene and overexpressing DR1087 gene was constructed.

Example 9: Construction of *Deinococcus Radiodurans* Mutant Strains Having Deletion of DR0861 Gene and Overexpressing DR1395 Gene A *Deinococcus radiodurans* mutant strain having deletion of DR0861 gene and overexpressing DR1395 gene was constructed by transfecting the DR07861 gene deficient *Deinococcus radiodurans* strain with a plasmid overexpressing DR1395 (crtE) gene known as a rate-limiting enzyme. The experiment was performed by the same manner as described in Example 7 except that the dr1395F1 (SEQ. ID. NO: 27) and dr1395R1 (SEQ. ID. NO: 28) primers listed in Table 3 were used to obtain DR1395 gene. As a result, a *Deinococcus radiodurans* mutant strain having deletion of DR0861 gene and overexpressing DR1395 gene was constructed.

Example 10: Construction of *Deinococcus Radiodurans* Mutant Strain Having Deletion of DR0861 Gene and Overexpressing DR1475 Gene A *Deinococcus radiodurans* mutant strain having deletion of DR0861 gene and overexpressing DR1475 gene was constructed by transfecting the DR07861 gene deficient *Deinococcus radiodurans* strain with a plasmid overexpressing DR1475 (dxs) gene known as a rate-limiting enzyme. The experiment was performed by the same manner as described in Example 7 except that the dr1475F1 (SEQ. ID. NO: 29) and dr1475R1 (SEQ. ID. NO: 30) primers listed in Table 3 were used to obtain DR1475 gene. As a result, a *Deinococcus radiodurans* mutant strain having deletion of DR0861 gene and overexpressing DR1475 gene was constructed.

Example 11: Construction of *Deinococcus Radiodurans* Mutant Strain Having Deletion of DR0861 Gene and Overexpressing DR0862 and Dr1087 Genes A *Deinococcus radiodurans* mutant strain having deletion of DR0861 gene and overexpressing DR0862 and DR1087 genes was constructed as follows.

First, PCR was performed to amplify the region containing groE promoter and DR1087 gene using the pRADZ3 plasmid comprising DR1087 gene constructed in Example 8 as a template with the groF (SEQ. ID. NO: 31) and dr1087R2 (SEQ. ID. NO: 32) primers listed in Table 4 below. Particularly, 1 µℓ of DNA template, 1 µℓ of each primer and 17 µℓ of sterile distilled water were all mixed, and then the mixture was added to pfu polymerase mix (Bioneer), followed by amplification using T-100 Thermal cycler DNA amplifier (Bio-rad). PCR was performed as follows: reacting at 95° C. for 5 minutes, and 30 cycles of reacting at 95° C. for 30 seconds, at 60° C. for 30 seconds and at 72° C. for 1 minute.

TABLE 4

| SEQ. ID. NO: | Name | Sequence (5'→3') |
|---|---|---|
| SEQ. ID. NO: 31 | groF | ataggcggccgctcggcttggaagcacgtatt |
| SEQ. ID. NO: 32 | dr1087R2 | gttacctaggcttgcagagggggtcccttta |

TABLE 4-continued

| SEQ. ID. NO: | Name | Sequence (5'→3') |
|---|---|---|
| SEQ. ID. NO: 33 | dr1395R2 | ctaggtcgaccttaagcctaggtcacttct cccgcgtcgcca |
| SEQ. ID. NO: 34 | dr1475R2 | gttacctaggctacacctcaatcggcacgt |

The obtained PCR product was electrophoresed on 1% agarose gel, followed by purification using a DNA fragment purification kit (Intron lifetechnology). The purified PCR product and the pRADZ3 plasmid containing DR0862 gene constructed in Example 7 were digested with NotI and SalI, and then ligated to construct a plasmid to express groE promoter and DR1087 at the downstream of the DR0862 gene in pRADZ3. The DR0862 deficient strain prepared in Example 6 was transfected with the constructed plasmid by the same manner as described in Example <3-4>. As a result, a *Deinococcus radiodurans* mutant strain having deletion of DR0861 gene and overexpressing DR0862 and DR1087 genes was constructed.

Example 12: Construction of *Deinococcus Radiodurans* Mutant Strain Having Deletion of DR0861 Gene and Overexpressing DR0862 and Dr1395 Genes A *Deinococcus radiodurans* mutant strain having deletion of DR0861 gene and overexpressing DR0862 and DR1395 genes was constructed. The experiment was performed by the same manner as described in Example 11 except that the pRADZ3 plasmid containing DR1395 gene as a template and the groF (SEQ. ID. NO: 31) and dr1395R2 (SEQ. ID. NO: 33) primers listed in Table 4 were used. As a result, a *Deinococcus radiodurans* mutant strain having deletion of DR0861 gene and overexpressing DR0862 and DR1395 genes was constructed.

Example 13: Construction of *Deinococcus Radiodurans* Mutant Strain Having Deletion of DR0861 Gene and Overexpressing DR0862 and Dr1475 Genes A *Deinococcus radiodurans* mutant strain having deletion of DR0861 gene and overexpressing DR0862 and DR1475 genes was constructed. The experiment was performed by the same manner as described in Example 11 except that the pRADZ3 plasmid containing DR1475 gene as a template and the groF (SEQ. ID. NO: 31) and dr1475R2 (SEQ. ID. NO: 34) primers listed in Table 4 were used (FIG. 10). As a result, a *Deinococcus radiodurans* mutant strain having deletion of DR0861 gene and overexpressing DR0862 and DR1475 genes was constructed.

Experimental Example 2: Confirmation of Phytoene Producibility of *Deinococcus Radiodurans* Mutant Strain Having Deletion of DR0861 Gene and Overexpressing DR0862, DR1087, DR1395 or DR1475 Gene <2-1> Culture of Strain and Obtainment of Culture Product First, pH of the culture medium comprising the constituents listed in Table 5 was adjusted to 7.0, followed by autoclaving.

TABLE 5

| Constituent | Final Conc. |
|---|---|
| Phosphate buffer | 20 mM |
| Ammonium sulfate | 15 mM |
| $MnCl_2$ | 5 μM |
| $MgCl_2$ | 0.8 mM |
| $CaCl_2$ | 0.18 mM |
| Fructose | 10 g/ℓ |
| Vitamin mix | 10 mg/mℓ |
| L-cystein | 50 mg/ℓ |
| L-methionine | 25 mg/ℓ |
| L-histidine | 25 mg/ℓ |
| Yeast extract | 1 g/ℓ |

The prepared liquid medium (50 mℓ) was distributed in a 250 mℓ Erlenmeyer flask, which was inoculated with 500 μℓ of each mutant strain prepared in Examples 6-13. The strain was cultured at 30° C., 200 rpm for 72 hours with stirring. At this time, chloramphenicol was added to the culture medium containing the strains prepared in Examples 7-13 at the concentration of 3 μg/mℓ, respectively. Upon completion of the culture, cells were recovered from the culture medium by centrifugation at 4° C., 4,000 rpm for 15 minutes, and then the supernatant was eliminated. The recovered cells were washed with tertiary distilled water, and the cells were suspended in 3 mℓ of an organic solvent comprising methanol and acetone (2:7, v/v). The suspended cells were allowed to stand at room temperature for 15 minutes to extract phytoene from the cells. 15 minutes later, the suspended cells were centrifuged at 4° C., 4000 rpm for 15 minutes to obtain supernatant. 1 mℓ of the obtained supernatant was filtered using a filter paper having a pore size of 0.2 μm. As a result, a solvent containing phytoene was finally obtained.

<2-2> Confirmation of Phytoene Producibility Through High Performance Liquid Chromatography (HPLC)

Figure 11:
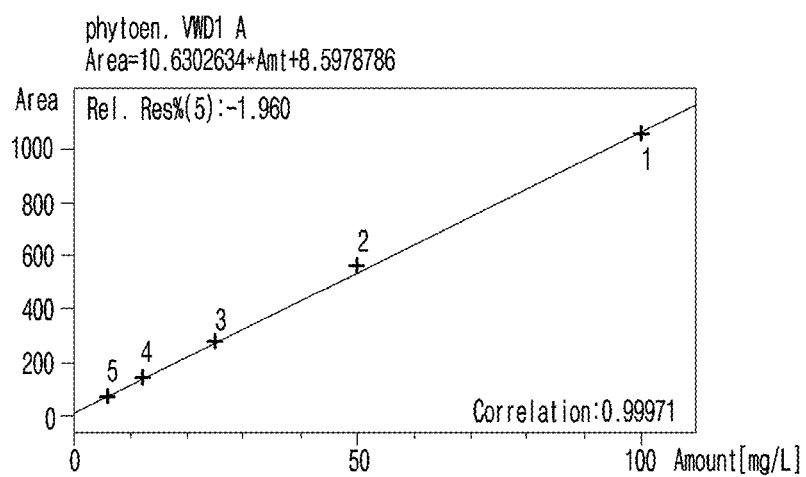
FIG. 11 is a graph illustrating the calibration curve prepared using the standard 15-cis-phytoene.
Figure 12:
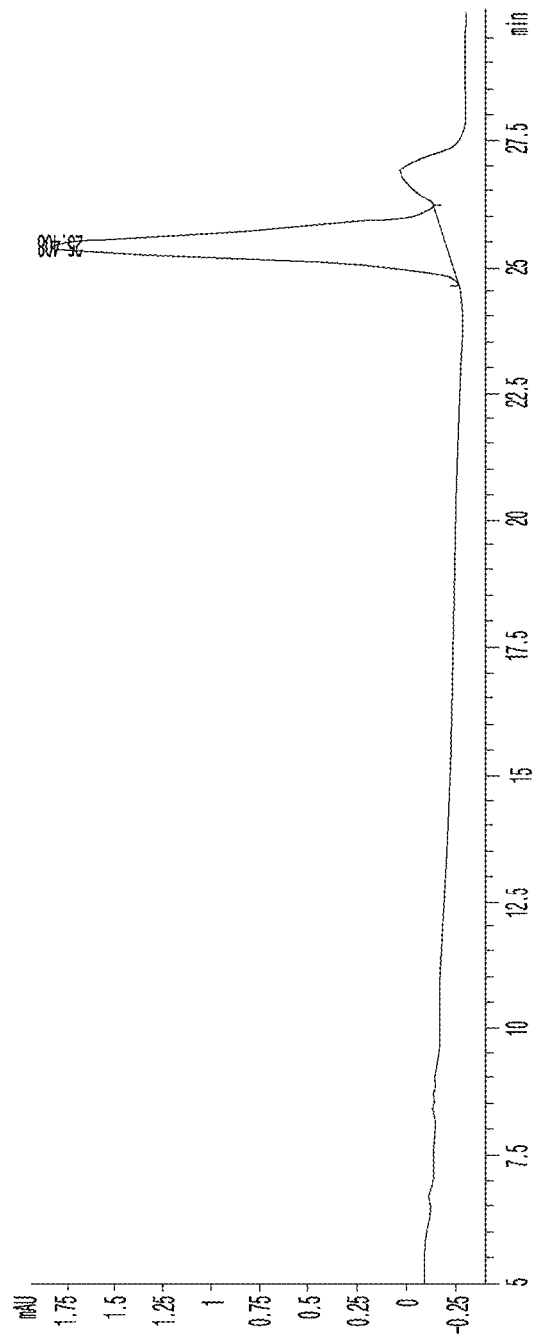
FIG. 12 is a chromatogram of HPLC performed using the standard 15-cis-phytoene.

The phytoene producibility was analyzed by HPLC using the residues obtained in Experimental Example <2-1> from the *Deinococcus radiodurans* mutant strains constructed in Examples 6-13 by the same manner as described in Experimental Example <1-2>. At this time, 15-cis-phytoene (>95%, Toronto Research Chemical) was used as a standard for comparison, and a calibration curve was prepared by diluting thereof from the concentration of 100 mg/ℓ to 6.25 mg/ℓ (FIG. 11 and FIG. 12). The phytoene producibility of the *Deinococcus radiodurans* mutant strains constructed in Examples 6-13, calculated using the prepared calibration curve, was shown in FIG. 13.

As shown in FIG. 13, the mutant strains constructed in Examples 7-13 produced higher amount of phytoene than the mutant strain of Example 6 (none, 0.34±0.15 mg/ℓ). In particular, among the mutant strains overexpressing only one gene, the mutant strain of Example 7 produced the highest amount of phytoene (1.85±0.18 mg/ℓ). Meanwhile, among the mutant strains overexpressing two genes, the mutant strain of Example 13 (dr0862$^+$, dr1475$^+$) produced the highest amount of phytoene (3.25±0.21 mg/ℓ) (FIG. 13).

<2-3> Confirmation of Phytoene Production According to Culture Time

The amount of phytoene produced according to the culture time was investigated using the mutant strain of Example 13 confirmed to produce the highest amount of phytoene in Experimental Example <2-2>. Culture products were obtained by the same manner as described in Experimental Example <2-1> except that the culture was performed respectively for 0, 24, 48, 72 and 96 hours. In addition, the phytoene producibility was investigated by the same manner as described in Experimental Example <2-2>.

Figure 14:
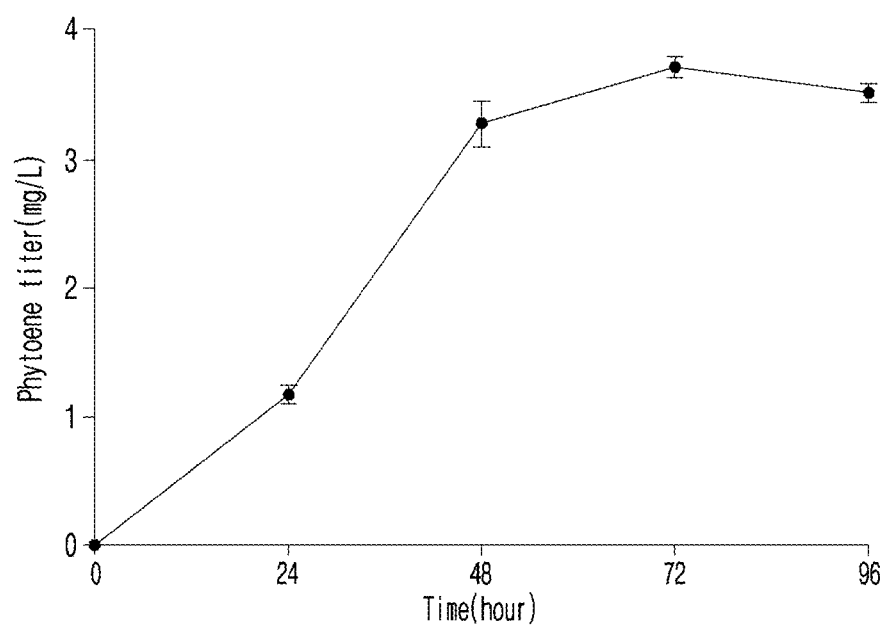
FIG. 14 is a graph illustrating the time dependent phytoene producibility of the mutant strain prepared in Example 13.

As a result, as shown in FIG. 14, phytoene production rapidly increased 24 hours after the culture started and reached the highest producibility 72 hours later (3.71±0.1 mg/ℓ). Thereafter, the production decreased slightly (FIG. 14).

Example 14: Construction of *Deinococcus Radiodurans* Mutant Strain Having Deletion of DR0861 and DR2250 Gene and Overexpressing DR0862 and DR1475 Genes First, PCR was performed by the same manner as described in Example 1 except that the primers listed in Table 6 below were used. As a result, 1 kb PCR products of the upstream and downstream regions of DR2250 gene were obtained, respectively.

TABLE 6

| SEQ. ID. NO: | Name | Sequence (5'→3') |
|---|---|---|
| SEQ. ID. NO: 35 | dr2250-1 | catgttcatcaccagccgca |
| SEQ. ID. NO: 36 | dr2250-2 | agcttatcgataccgtcgactgtagcggga gcagtatcac |
| SEQ. ID. NO: 37 | dr2250-3 | gtgatactgctcccgctacagtcgacggta tcgataagct |
| SEQ. ID. NO: 38 | dr2250-4 | aatgccttctcgccatccagcatgcctgca ggtcgactct |
| SEQ. ID. NO: 39 | dr2250-5 | agagtcgacctgcaggcatgctggatggcg agaaggcatt |
| SEQ. ID. NO: 40 | dr2250-6 | gatgtcgcgagttcgaatct |

The obtained PCR products were linked to kanamycin resistant gene by the same manner as described in Examples <3-2> and <3-3>. A mutant strain having deletion of DR0861 and DR2250 genes was constructed using the DR0861 deficient mutant strain constructed in Example 6 by the same manner described in Example <3-4>. The prepared strain was transfected with a plasmid containing DR0862 AND DR1475 genes by the same manner as described in Example <3-4>. As a result, a *Deinococcus radiodurans* mutant strain having deletion of DR0861 and DR2250 genes but overexpressing DR0862 and DR1475 genes was constructed.

Comparative 3: Construction of *Deinococcus Radiodurans* Mutant Strain Having Deletion of DR0861 and DR2250 Genes A *Deinococcus radiodurans* mutant strain having deletion of DR0861 and DR2250 genes was constructed using the PCR product containing the kanamycin resistant gene and the upstream and downstream regions of DR2250 obtained in Example 14 and the DR0861 deficient mutant strain constructed in Example 6 by the same manner as described in Example <3-4>.

Experimental Example 3: Confirmation of Phytoene Producibility of *Deinococcus Radiodurans* Mutant Strain Having Deletion of DR0861 and DR2250 Genes but Overexpressing DR0862 and DR1475 Genes <3-1> Confirmation of Phytoene Producibility Through High Performance Liquid Chromatography (HPLC)

Phytoene production in the mutant strains constructed in Examples 6, 13 and 14 and in Comparative Example 3 was investigated by the same manner as described in Experimental Example 2. As a result, the phytoene producibility of the mutant strains constructed in Examples 6, 13 and 14 and in Comparative Example 3 was shown in FIG. 15.

Figure 15:
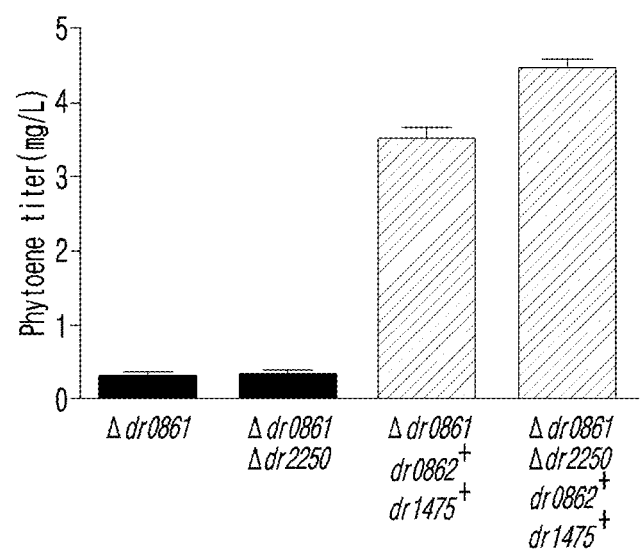
FIG. 15 is a graph illustrating the quantification of the phytoene producibility of the mutant strains prepared in Examples 6, 13 and 14 and Comparative Example 3, measured by HPLC (Δdr0861: Example 6; Δdr0861, Δdr2250: Comparative Example 3; Δdr0861, dr0862+, dr1475+: Example 13; Δdr0861, Δdr2250, dr0862+, dr1475+: Example 14).

As shown in FIG. 15, the mutant strains prepared in Examples 13 and 14 demonstrated higher phytoene producibility than the mutant strains prepared in Examples 6 and Comparative Example 3. In particular, the mutant strain prepared in Example 14 (4.5±0.2 mg/ℓ) displayed 21% increased phytoene production amount by the mutant strain prepared in Example 13 (3.5±0.24 mg/ℓ) (FIG. 15).

<3-2> Confirmation of Phytoene Production According to Culture Time

The amount of phytoene produced according to the culture time was investigated by the same manner as described in Experimental Example <2-3> using the mutant strain of Example confirmed to produce the highest amount of phytoene in Experimental Example <3-1>.

Figure 16:
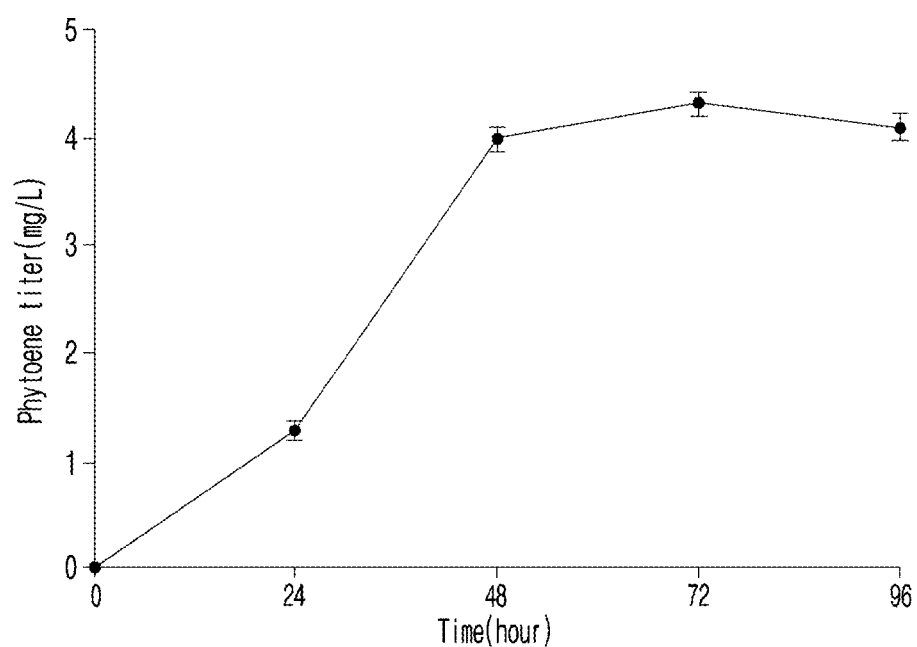
FIG. 16 is a graph illustrating the time dependent phytoene producibility of the mutant strain prepared in Example 14.

As a result, as shown in FIG. 16, phytoene producibility was the highest at 72 hours of culture, which was similar to the result of confirming the amount of phytoene production over the time using the mutant strain of Example 13 (FIG. 16).

<3-3> Comparative Analysis of Strain Growth, Carbon Source Consumption, and Phytoene Production Using the mutant strain prepared in Example 14, the growth curve of the strain, the consumption ratio of the carbon source used for the growth and the amount of phytoene production were analyzed. The results are shown in FIG. 17.

Figure 17:
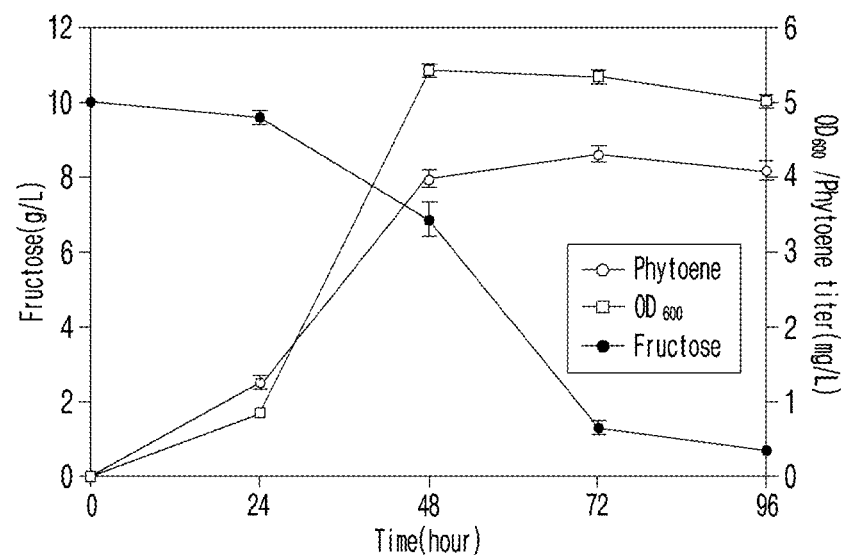
FIG. 17 is a graph illustrating the results of comparing the phytoene producibility of the mutant strain prepared in Example 14 with the growth curve of the strain and the consumption ratio of the carbon source included in the culture medium.

As shown in FIG. 17, the strain of Example 14 consumed almost all the carbon source contained in the culture medium for 96 hours of culture, and showed maximum cell growth for 48 hours of culture ($OD_{600}$=5.4±0.1). In addition, the highest phytoene production was observed 72 hours after the culture started (4.3±0.1 mg/ℓ) (FIG. 17). That is, it was confirmed based on the results above that the mutant strain of Example 14 produced phytoene approximately 600 μg/ℓ per hour for 72 hours during the culture.

What is claimed is:

1. A method for preparing a *Deinococcus* species mutant strain having a deletion of DR0861 gene using cre-lox system, which comprises the following steps:

1) deleting DR0861 gene by introducing a DNA construct in which the upstream and downstream fragments of DR0861 gene were fused to both ends of the lox nucleic acid fragment containing a first selection marker in a *Deinococcus* species strain, wherein the lox nucleic acid fragment is a polynucleotide composed of the nucleotide sequence represented by SEQ ID NO: 17;

2) deleting the first selection marker by introducing a vector comprising a groE promoter, a gene encoding cre recombinase, a second selection marker and a temperature sensitive repUts in the strain having deletion of DR0861 gene of step 1), wherein the vector is a polynucleotide composed of the nucleotide sequence represented by SEQ ID NO: 21; and 3) eliminating the vector comprising the second selection marker by culturing the prepared mutant strain obtained in step 2).

2. The method for preparing the *Deinococcus* species mutant strain having deletion of DR0861 gene according to claim 1, wherein the DR0861 gene is a polynucleotide composed of the nucleotide sequence represented by SEQ. ID. NO: 22.

3. The method for preparing the *Deinococcus* species mutant strain having deletion of DR0861 gene according to claim 1, wherein the culture of step 3) is performed at a temperature range of 30° C. to 40° C.

4. The method for preparing the *Deinococcus* species mutant strain having deletion of DR0861 gene according to claim 1, wherein the *Deinococcus* species strain is *Deinococcus radiodurans*.

5. The method for preparing the *Deinococcus* species mutant strain having deletion of DR0861 gene according to claim 1, wherein the upstream and downstream fragments of the DR0861 gene have a length of 0.5 to 1.2 kb.

6. The method for preparing the *Deinococcus* species mutant strain having deletion of DR0861 gene according to claim 1, wherein the lox nucleic acid fragment contains one or more lox genes selected from the group consisting of lox71 and lox66 at both ends of the fragment.

7. The method for preparing the *Deinococcus* species mutant strain having deletion of DR0861 gene according to claim 1, wherein the groE promoter is a polynucleotide comprising the nucleotide sequence represented by SEQ. ID. NO: 19.

8. The method for preparing a *Deinococcus* species mutant strain having deletion of DR0861 gene according to claim 1, the wherein the first and second selection markers are antibiotic resistance genes.

9. The method for preparing the *Deinococcus* species mutant strain having deletion of DR0861 gene according to claim 8, wherein the antibiotic resistance gene is one or more genes selected from the group consisting of kanamycin, chloramphenicol, spectinomycin and streptomycin resistant genes.

10. The method for preparing the *Deinococcus* species mutant strain having deletion of DR0861 gene according to claim 1, wherein the first selection marker is eliminated by the expression of cre recombinase.

11. The method for preparing the *Deinococcus* species mutant strain having deletion of DR0861 gene according to claim 1, wherein the method further comprises the step of introducing a plasmid expressing one or more genes selected from the group consisting of DR0862, DR1087, DR1395 and DR1475.

12. The method for preparing the *Deinococcus* species mutant strain having deletion of DR0861 gene according to claim 11, wherein the method further comprises the step of introducing both plasmids expressing DR0862 and DR1475 genes, respectively.

13. The method for preparing the *Deinococcus* species mutant strain having deletion of DR0861 gene according to claim 1, wherein the method further comprises the step of deleting DR2250 gene.

14. A *Deinococcus* species mutant strain having deletion of DR0861 gene but having phytoene producibility wherein the *Deinococcus* species mutant strain has been prepared by the method of claim 1.

15. A method for producing phytoene comprising the step of culturing the mutant strain of claim 14 to produce the phytoene.

16. The method for preparing the *Deinococcus* species mutant strain having deletion of DR0861 gene according to claim 11, wherein the method further comprises the step of deleting DR2250 gene.

17. The method for preparing the *Deinococcus* species mutant strain having deletion of DR0861 gene according to claim 12, wherein the method further comprises the step of deleting DR2250 gene.

* * * * *

SEQUENCE LISTING

<160> NUMBER OF SEQ ID NOS: 45

<210> SEQ ID NO 1
<211> LENGTH: 44
<212> TYPE: DNA
<213> ORGANISM: Artificial Sequence
<220> FEATURE:
<223> OTHER INFORMATION: Lox66F DNA sequence

<400> SEQUENCE: 1
gcttgatatc taccgttcgt atagcataca ttatacgaag ttat                44

<210> SEQ ID NO 2
<211> LENGTH: 44
<212> TYPE: DNA
<213> ORGANISM: Artificial Sequence
<220> FEATURE:
<223> OTHER INFORMATION: Lox71R DNA sequence

<400> SEQUENCE: 2
tagaggatcc taccgttcgt ataatgtatg ctatacgaag ttat                44

<210> SEQ ID NO 3
<211> LENGTH: 32
<212> TYPE: DNA
<213> ORGANISM: Artificial Sequence
<220> FEATURE:
<223> OTHER INFORMATION: GroES DNA sequence

<400> SEQUENCE: 3
cgtggcggcc gctcggcttg gaagcacgta tt                             32

<210> SEQ ID NO 4
<211> LENGTH: 41
<212> TYPE: DNA
<213> ORGANISM: Artificial Sequence
<220> FEATURE:
<223> OTHER INFORMATION: GroER DNA sequence

<400> SEQUENCE: 4
tacgggcagt aaattggaca tatccactag taacggccgc c                   41

<210> SEQ ID NO 5
<211> LENGTH: 41
<212> TYPE: DNA
<213> ORGANISM: Artificial Sequence
<220> FEATURE:
<223> OTHER INFORMATION: CreF DNA sequence

<400> SEQUENCE: 5
ggcggccgtt actagtggat atgtccaatt tactgcccgt a                   41

<210> SEQ ID NO 6
<211> LENGTH: 40
<212> TYPE: DNA
<213> ORGANISM: Artificial Sequence
<220> FEATURE:
<223> OTHER INFORMATION: CreR DNA sequence

<400> SEQUENCE: 6
agcttatcga taccgtcgac ctaatcgcca tcttccagca                     40

<210> SEQ ID NO 7
<211> LENGTH: 40
<212> TYPE: DNA
<213> ORGANISM: Artificial Sequence

```
<220> FEATURE:
<223> OTHER INFORMATION: pKatF DNA sequence

<400> SEQUENCE: 7
tgctggaaga tggcgattag gtcgacggta tcgataagct          40

<210> SEQ ID NO 8
<211> LENGTH: 40
<212> TYPE: DNA
<213> ORGANISM: Artificial Sequence
<220> FEATURE:
<223> OTHER INFORMATION: pKatR DNA sequence

<400> SEQUENCE: 8
ccagtgattt ttttctccat atgctctcct tcgcctcgct          40

<210> SEQ ID NO 9
<211> LENGTH: 40
<212> TYPE: DNA
<213> ORGANISM: Artificial Sequence
<220> FEATURE:
<223> OTHER INFORMATION: CmK DNA sequence

<400> SEQUENCE: 9
agcgaggcga aggagagcat atggagaaaa aaatcactgg          40

<210> SEQ ID NO 10
<211> LENGTH: 30
<212> TYPE: DNA
<213> ORGANISM: Artificial Sequence
<220> FEATURE:
<223> OTHER INFORMATION: CmR DNA sequence

<400> SEQUENCE: 10
gcgactcgag gtcgactcta gaggatcctc          30

<210> SEQ ID NO 11
<211> LENGTH: 20
<212> TYPE: DNA
<213> ORGANISM: Artificial Sequence
<220> FEATURE:
<223> OTHER INFORMATION: primer 1 DNA sequence

<400> SEQUENCE: 11
catagtgaaa gaaacgtctg          20

<210> SEQ ID NO 12
<211> LENGTH: 40
<212> TYPE: DNA
<213> ORGANISM: Artificial Sequence
<220> FEATURE:
<223> OTHER INFORMATION: primer 2 DNA sequence

<400> SEQUENCE: 12
agcttatcga taccgtcgac gacagtaaac ctcggaagtc          40

<210> SEQ ID NO 13
<211> LENGTH: 40
<212> TYPE: DNA
<213> ORGANISM: Artificial Sequence
<220> FEATURE:
<223> OTHER INFORMATION: primer 3 DNA sequence

<400> SEQUENCE: 13
gacttccgag gtttactgtc gtcgacggta tcgataagct          40
```

<210> SEQ ID NO 14
<211> LENGTH: 40
<212> TYPE: DNA
<213> ORGANISM: Artificial Sequence
<220> FEATURE:
<223> OTHER INFORMATION: primer 4 DNA sequence

<400> SEQUENCE: 14
ttaagcggaa tccgtatgac catgcctgca ggtcgactct          40

<210> SEQ ID NO 15
<211> LENGTH: 40
<212> TYPE: DNA
<213> ORGANISM: Artificial Sequence
<220> FEATURE:
<223> OTHER INFORMATION: primer 5 DNA sequence

<400> SEQUENCE: 15
agagtcgacc tgcaggcatg gtcatacgga ttccgcttaa          40

<210> SEQ ID NO 16
<211> LENGTH: 20
<212> TYPE: DNA
<213> ORGANISM: Artificial Sequence
<220> FEATURE:
<223> OTHER INFORMATION: primer 6 DNA sequence

<400> SEQUENCE: 16
ttggtccaca tgctggtgca                                20

<210> SEQ ID NO 17
<211> LENGTH: 1060
<212> TYPE: DNA
<213> ORGANISM: Artificial Sequence
<220> FEATURE:
<223> OTHER INFORMATION: lox nucleic acid fragment DNA sequence

<400> SEQUENCE: 17
gtcgacggta tcgataagct tgatatctac cgttcgtata gcatacatta tacgaagtta      60
tgaattcgag ctcgcatgga gaccgagggc ccttgacatt gagaatgatt ctcaatatgg     120
tgcagggagc ttcgggcctc ttgccgcgca gcagagccag cgaggcgaag gagagcatat     180
gagccatatt caacgggaaa cgtcttgctc gaagccgcga ttaaattcca acatggatgc     240
tgatttatat gggtataaat gggctcgcga taatgtcggg caatcaggtg cgacaatcta     300
tcgattgtat gggaagcccg atgcgccaga gttgtttctg aaacatggca aaggtagcgt     360
tgccaatgat gttacagatg agatggtcag actaaactgg ctgacggaat ttatgcctct     420
tccgaccatc aagcatttta tccgtactcc tgatgatgca tggttactca ccactgcgat     480
ccccgggaaa acagcattcc aggtattaga agaatatcct gattcaggtg aaaatattgt     540
tgatgcgctg gcagtgttcc tgcgccggtt gcattcgatt cctgtttgta attgtccttt     600
taacagcgat cgcgtatttc gtctcgctca ggcgcaatca cgaatgaata cggtttggt      660 tgatgcgagt gattttgatg acgagcgtaa tggctggcct gttgaacaag tctggaaaga     720
aatgcataag cttttgccat ctcaccgga ttcagtcgtc actcatggtg atttctcact     780
tgataacctt attttgacg aggggaaatt aataggttgt attgatgttg acgagtcgg      840 aatcgcagac cgataccagg atcttgccat cctatggaac tgcctcggtg agttttctcc     900
ttcattacag aaacggcttt ttcaaaaata tggtattgat aatcctgata tgaataaatt     960
gcagtttcat ttgatgctcg atgagttttt ctaatcaata acttcgtata gcatacatta    1020

```
tacgaacggt aggatcctct agagtcgacc tgcaggcatg                         1060
```

<210> SEQ ID NO 18
<211> LENGTH: 340
<212> TYPE: DNA
<213> ORGANISM: Artificial Sequence
<220> FEATURE:
<223> OTHER INFORMATION: groE promoter DNA sequence
<400> SEQUENCE: 18

```
ttggaagcac gtattgtcgc cctacatata tacgttaaag ctaacagctg gcaaggggat     60
accccattc cccgtcccag cgccccttga gcgtcataga ctcagattgt cagcttcggt    120
cagttgacat ttttcttatc ggcgctctac catccgtgac ggattgaagg cgctgggcgg    180
gaaaaagctc gccggcacga ctctccgcca ttccatctca ctcacaggag accccacat    240
gctgaaacct ttaggcgacc gcgttctggt tgaaattatc gaagaagccg agcagaagac    300
aagccgaatt ccagcacact ggcggccgtt actagtggat                         340
```

<210> SEQ ID NO 19
<211> LENGTH: 93
<212> TYPE: DNA
<213> ORGANISM: Artificial Sequence
<220> FEATURE:
<223> OTHER INFORMATION: Kat promoter DNA sequence
<400> SEQUENCE: 19

```
catggagacc gagggcccctt gacattgaga atgattctca atatggtgca gggagcttcg     60
ggcctcttgc cgcgcagcag agccagcgag gcg                                93
```

<210> SEQ ID NO 20
<211> LENGTH: 2336
<212> TYPE: DNA
<213> ORGANISM: Artificial Sequence
<220> FEATURE:
<223> OTHER INFORMATION: pAM1 plasmid DNA sequence
<400> SEQUENCE: 20

```
ggtaccgggc ccccctcga ggtcgacggt atcgataagc ttgatatcta ccgttcgtat     60
agcatacatt atacgaagtt atgaattcga gctcgcatgg agaccgaggg cccttgacat    120
tgagaatgat tctcaatatg gtgcagggag cttcgggcct cttgccgcgc agcagagcca    180
gcgaggcgaa ggagagcata tgagccatat tcaacgggaa acgtcttgct cgaagccgcg    240
attaaattcc aacatggatg ctgatttata tgggtataaa tgggctcgcg ataatgtcgg    300
gcaatcaggt gcgacaatct atcgattgta tgggaagccc gatgcgccag agttgtttct    360
gaaacatggc aaaggtagcg ttgccaatga tgttacagat gagatggtca gactaaactg    420
gctgacggaa tttatgcctc ttccgaccat caagcatttt atccgtactc ctgatgatgc    480
atggttactc accactgcga tccccgggaa aacagcattc caggtattag aagaatatcc    540
tgattcaggt gaaaatattg ttgatgcgct ggcagtgttc ctgcgccggt tgcattcgat    600
tcctgtttgt aattgtcctt ttaacagcga tcgcgtattt cgtctcgctc aggcgcaatc    660
acgaatgaat aacggtttgg ttgatgcgag tgattttgat gacgagcgta atggctggcc    720
tgttgaacaa gtctggaaag aaatgcataa gcttttgcca ttctcaccgg attcagtcgt    780
cactcatggt gatttctcac ttgataacct tatttttgac gaggggaaat taataggttg    840
tattgatgtt ggacgagtcg gaatcgcaga ccgataccag gatcttgcca tcctatggaa    900
```

```
ctgcctcggt gagttttctc cttcattaca gaaacggctt tttcaaaaat atggtattga    960
taatcctgat atgaataaat tgcagtttca tttgatgctc gatgagtttt tctaatcaat   1020
aacttcgtat agcatacatt atacgaacgg taggatcctc tagagtcgac ctgcaggcat   1080
gcaagcttgg cgtaatcatg gtcatagctg tttcctgtgt gaaattgtta tccgctcaca   1140
attccacaca acatacgagc cggaagcata agtgtaaag cctggggtgc ctaatgagtg   1200
agctaactca cattaattgc gttgcgctca ctgcccgctt tccagtcggg aaacctgtcg   1260
tgccagctgc attaatgaat cggccaacgc gcggggagag gcggtttgcg tattgggcgc   1320
tcttccgctt cctcgctcac tgactcgctg cgctcggtcg ttcggctgcg gcgagcggta   1380
tcagctcact caaaggcggt aatacggtta tccacagaat caggggataa cgcaggaaag   1440
aacatgtgag caaaaggcca gcaaaaggcc aggaaccgta aaaaggccgc gttgctggcg   1500 ttttccata ggctccgccc ccctgacgag catcacaaaa atcgacgctc aagtcagagg   1560
tggcgaaacc cgacaggact ataaagatac caggcgtttc cccctggaag ctccctcgtg   1620
cgctctcctg ttccgaccct gccgcttacc ggatacctgt ccgcctttct cccttcggga   1680
agcgtggcgc tttctcatag ctcacgctgt aggtatctca gttcggtgta ggtcgttcgc   1740
tccaagctgg gctgtgtgca cgaaccccc gttcagcccg accgctgcgc cttatccggt   1800
aactatcgtc ttgagtccaa cccggtaaga cacgacttat cgccactggc agcagccact   1860
ggtaacagga ttagcagagc gaggtatgta ggcggtgcta cagagttctt gaagtggtgg   1920
cctaactacg gctacactag aagaacagta tttggtatct gcgctctgct gaagccagtt   1980
accttcggaa aaagagttgg tagctcttga tccggcaaac aaaccaccgc tggtagcggt   2040
ggtttttttg tttgcaagca gcagattacg cgcagaaaaa aaggatctca agaagatcct   2100
ttgatctttt ctacggggtc tgacgctcag tggaacgaaa actcacgtta agggattttg   2160
gtcatggcca ttcgccattc aggctgcgca actgttggga agggcgatcg gtgcgggcct   2220
cttcgctatt acgccagctg gcgaaagggg gatgtgctgc aaggcgatta agttgggtaa   2280
cgccagggtt ttcccagtca cgacgttgta aaacgacggc cagtgaattc gagctc       2336
```

<210> SEQ ID NO 21
<211> LENGTH: 10227
<212> TYPE: DNA
<213> ORGANISM: Artificial Sequence
<220> FEATURE:
<223> OTHER INFORMATION: pAM2 plasmid DNA sequence

<400> SEQUENCE: 21

```
tgtctaacaa ttcgttcaag ccgacgccgc ttcgcggcgc ggcttaactc aagcgttaga     60
tgcactaagc acataattgc tcacagcctc gcgaaccatc aagcttatcg ataccgtcga    120
ggaacctctt acgtgccaat caacgtctca ttttcgccaa aagttggccc agggcttccc    180
ggtatcaaca gggacaccag gatttattta ttctgcgaag tgatcttccg tcacaggtat    240
ttattcggtc gaaaaggatc taggtgaaga tcctttttga taatctcatg accaaaatcc    300
cttaacgtga gttttcgttc cactgagcgt cagaccccgt agaaaagatc aaaggatctt    360
cttgagatcc ttttttttctg cgcgtaatct gctgcttgca acaaaaaaaa ccaccgctac    420
cagcggtggc ttgtttgccg gatcaagagc taccaactct ttttccgaag gtaactggct    480
tcagcagagc gcagatacca atactgttc ttctagtgta gccgtagtta ggccaccact    540
tcaagaactc tgtagcaccg cctacagacc tcgctctgct aatcctgtta ccagtggctg    600
ctgccagtgg cgataagtcg tgtcttaccg ggttggactc aagacgatag ttaccggata    660
```

```
aggcgcagcg gtcgggctga acgggggtt  cgtgcacaca gcccagcttg gagcgaacga    720
cctacaccga actgagatac ctacagcgtg agctatgaga aagcgccacg cttcccgaag    780
ggagaaaggc ggacaggtat ccggtaagcg gcagggtcgg aacaggagag cgcacgaggg    840
agcttccagg gggaaacgcc tggtatcttt atagtcctgt cgggtttcgc cacctctgac    900
ttgagcgtcg attttgtga tgctcgtcag ggggcggag  cctatggaaa acgccagca     960 acgcggcctt tttacggttc ctggcctttt gctggctttt tgctcacatg ttctttcctg   1020
cgttatcccc tgattctgtg ataaccgta ttaccgcctt tgagtgagct gataccgctc    1080
gccgcagccg aacgaccgag cgcagcgagt cagtgagcga ggaagcggaa gaggatctag   1140
cacaagagcg gaaagatgtt ttgttctaca tccagaacaa cctctgctaa aattcctgaa   1200
aaattttgca aaaagttgtt gactttatct acaaggtgtg gcataatgtg tggaattgtg   1260
agcgctcaca attaagcttg aattcccggg cggccgctcg gcttggaagc acgtattgtc   1320
gccctacata tatacgttaa agctaacagc tggcaagggg ataccccat  tccccgtccc   1380 agcgcccctt gagcgtcata gactcagatt gtcagcttcg gtcagttgac attttctta   1440 tcggcgctct accatccgtg acggattgaa ggcgctgggc gggaaaaagc tcgccggcac   1500
gactctccgc cattccatct cactcacagg aggacccac  atgctgaaac ctttaggcga   1560
ccgcgttctg gttgaaatta tcgaagaagc cgagcagaag acaagccgaa ttccagcaca   1620
ctggcggccg ttactagtat gtccaattta ctgcccgtac accaaaattt gcctgcatta   1680
ccggtcgatg caacgagtga tgaggttcgc aagaacctga tggacatgtt cagggatcgc   1740
caggcgtttt ctgagcatac ctggaaaatg cttctgtccg tttgccggtc gtgggcggca   1800
tggtgcaagt tgaataaccg gaaatggttt cccgcagaac ctgaagatgt tcgcgattat   1860
cttctatatc ttcaggcgcg cggtctggca gtaaaaacta tccagcaaca tttgggccag   1920
ctaaacatgc ttcatcgtcg gtccgggctg ccacgaccaa gtgacagcaa tgctgtttca   1980
ctggttatgc ggcggatccg aaaagaaaac gttgatgccg gtgaacgtgc aaaacaggct   2040
ctagcgttcg aacgcactga tttcgaccag gttcgttcac tcatggaaaa tagcgatcgc   2100
tgccaggata tacgtaatct ggcatttctg gggattgctt ataacaccct gttacgtata   2160
gccgaaattg ccaggatcag ggttaaagat atctcacgta ctgacggtgg gagaatgtta   2220
atccatattg gcagaacgaa aacgctggtt agcaccgcag gtgtagagaa ggcacttagc   2280
ctgggggtaa ctaaactggt cgagcgatgg atttccgtct ctggtgtagc tgatgatccg   2340
aataactacc tgttttgccg ggtcagaaaa atggtgttg  ccgcgccatc tgccaccagc   2400
cagctatcaa ctcgcgccct ggaagggatt tttgaagcaa ctcatcgatt gatttacggc   2460
gctaaggatg actctggtca gagatacctg gcctggtctg gacacagtgc ccgtgtcgga   2520
gccgcgcgag atatggcccg cgctggagtt tcaataccgg agatcatgca agctggtggc   2580
tggaccaatg taaatattgt catgaactat atccgtaacc tggatagtga acaggggca    2640 atggtgcgcc tgctggaaga tggcgattag gtcgacggta tcgataagct tgatatcgaa   2700
ttcgagctcg catggagacc gagggcccct gacattgaga atgattctca atatggtgca   2760
gggagcttcg ggcctcttgc cgcgcagcag agccagcgag gcgaaggaga gcatatggag   2820
aaaaaaatca ctggatatac caccgttgat atatcccaat ggcatcgtaa agaacatttt   2880
gaggcatttc agtcagttgc tcaatgtacc tataaccaga ccgttcagct ggatattacg   2940 gccttttaa  agaccgtaaa gaaaaataag cacaagtttt atccggcctt tattcacatt   3000
```

-continued

```
cttgcccgcc tgatgaatgc tcatccggaa ttccgtatgg caatgaaaga cggtgagctg    3060
gtgatatggg atagtgttca cccttgttac accgttttcc atgagcaaac tgaaacgttt    3120
tcatcgctct ggagtgaata ccacgacgat ttccggcagt ttctacacat atattcgcaa    3180
gatgtggcgt gttacggtga aaacctggcc tatttcccta aagggtttat tgagaatatg    3240
tttttcgtct cagccaatcc ctgggtgagt ttcaccagtt ttgatttaaa cgtggccaat    3300
atggacaact tcttcgcccc cgttttcacg atgggcaaat attatacgca aggcgacaag    3360
gtgctgatgc cgctggcgat tcaggttcat catgccgttt gtgatggctt ccatgtcggc    3420
agaatgctta atgaattaca acagtactgc gatgagtggc agggcggggc gtaattttt    3480 taaggcagtt attggtgccc ttaaacgcct ggttgctacg cctgaataag tgataataag    3540
cggatgaatg gcagaaattc gtcgaagctc tagaggatcc tctagagtcg acctcgagtt    3600
cgcgaacggc cggagaaaaa atccccccgg tggcaatccg gggggttttt tctcggatct    3660
tactttgatt ttagtacaaa aaatgaattt cattacaaac aggctttaac gaaaaaggaa    3720
gagttgcaag ccgcgctaga tggcctgaca gctggtagat accgcattat tatccgcctc    3780
atacaaccaa cggggcaccc catccaacat tcgcagcagg tggaagaaga taaccaatcg    3840
cagggacaaa ctcagctgga cgaaatctct tttgaaaccg acgcagacgc cgagttttaa    3900
gtttttgaag tctgcgcgac catccccagc cccaccacat cgggcaacgc tgccgccgcc    3960
gccgccacgc gccgggtgtc ggtctgcgcg taaatcatgg tcgtttgaat gttctcatgg    4020
cccagcaact ctttgatttc gtcgagcgtc cgcccgttat tgagcaacgt ggtggcgaac    4080
gtgtgccgca gcttgtgcgg gctgacggtg gcccgggtcga ggcccgcacg ctcggcggcg    4140
gtgtcgagca tcttgccgat ggtccgggcc tgcatttgtt ggccgtacct tttccccgac    4200
agcggcgacc atacccaggg cgtgaccggg ttccgtgcg tcttgcgctc cctgagccag    4260
cgcatcagcg cccttgtgc agtgggcgag agcggcacgc gcctttcctt gtcgcccttg    4320
ccgatgacgc gcacgcgac gggcgagccg tcctgatact cgatgtccgc gaacttcatc    4380
gccagcattt cggagatgcg gaggcccgtc ccgtacagga aagcgacaat gcaccagttt    4440
ttcagcccgc gctgggggga cttgtcgcgg taaacgactt ctagcagctt ggacacgtcc    4500
tccagggtga gtttgaccgg ggcgcgtttc ggaatcttcg gggtggtcag gtcggcggtg    4560
atgtcctgca cgccgggcag cttttgcacg cgcaccagaa accgccagaa cgaacgccag    4620
gagttcacca gtcggtgaaa cgccggggc gatgggtcgg cggcagccag gaaagcccgc    4680
aggtcggcgg cggagagttc cccccagtcg cgcccgcgca agtgctgggg cttgtcctcg    4740
gcgtccagcc aggagcggag cagccgaaca tctttcaggt actcgcgcac ggtggccgga    4800
ctgcgcccct gttccttcgc caagtagtgc gcccagattt caatttgatt ctgtgcagac    4860
attcaaacct cctagtggtc tggggtcgcc cagcgggggg caattttagc tattttactg    4920
aaaataataa ttttccgcct ttagacttag ccactcagac cgaaggcgca accgtccca    4980 gacagcaaat aagccgcatt aaggggggtc ggcgcggggt tccctgcacc caactttacg    5040
gaaaataatt cagctttacg gaaaataaca cgttgggaaa ggtaagaag gggttaagcc    5100 ttgttgcatg gtctggcatg gttaagcaaa ctggggtat gcctcccaag tcaagcaagc    5160
ccaagccagc gcccgccgtg ctgcccgctg acctctcggc ggtggccttc gtgaccgatg    5220
ctcaggcggc ggcttacctg gggctgtcca tccgctcggc acggtacttg gtcgaagaag    5280
gcaaactgaa acgggtctac cctcgcccgc gtgcggcccg catcaccgcc gagagcctga    5340
ccgggtacag gcaggccata aagaaggtc gcccgccccg aatctggacg cagccgggca    5400
```

-continued

```
atgtccacac gcccgcgccc gctgcaccag cacccgcgcc ggagaagaag aagggctgc      5460 tttcccggtg gggcctgggc gggggctaaa acctaagcag gctgcatggc acagcttttt      5520
gtttcacagt tcttgcgctg tagtagcaac tttagaacta ggcgatgtca tctgaaaaaa      5580
gctgggtttt agcatatttc agaagagaat cgtacgcctc agctaccatt cttgcagccg      5640
cgttcagggt cttgacgtgt tctttgtatc tatcagcaaa ctgagaaccc aattctggat      5700
catccttgta acgccaactc tccgaccatt ccgaaggaac gccttgtagt cctcctgagc      5760
cgttagggta tgtctttagt ccaatcaaat gggacatttg cagacaggaa cgcacaagtg      5820
tctcacgtcg cttctctatt tcaatatcta aaaattcttc actcttatcg ttgcttgaca      5880
tattaaaact gtctaactga tccagttcac ttatatggaa agtatcacta aagtcatggc      5940
ttctcagaaa ttcaatactt cccattgatg gggaccggtt aaccaaatcg ataaaaattt      6000
ttctgtcatg tttcagataa gttttggcg cgttgatttt ataataaagc cgccattctt      6060
gtgccaacaa cgccacgaaa agagccacag cagcagcggc cacatcccat tgaaaatctt      6120
tcgccagacc aaccgccagg agaaccaagc cgaaatagtt agcccagcga actaaaaaac      6180
tatctataaa cgtattaaga aacgttcggg tcatatttcc gtgaatcata tcaggacgta      6240
aatttgcaca tgacgcattt ccgggggctt ttatccctcg gacttctttt caggccctt      6300 ctcggccttt ctgtgaccct gttttttcag gccgcgaact gcgcctggtc gggcctgacc      6360
cccacacgct ggccttcgta ctcacgcagc ctgcccagca ggtcggccag cgcggcattg      6420 accacgcgg cgaggttgcg gggcggcgtt ccgcctgcgg tctggtcgtg cttcacgtcg      6480
cgcagcacgc gcaccagcac cgcgcccacg tcgtcggaca cgtcccggcc agcgtcggcg      6540
gcgcgggtga tgttccaaat gagtttccgc cagaagccca gcgagtcggc cccgtccccg      6600
aaagctgccg ctagcgcccg cgcctgcctg tccgcgatct cggcgcggta ggccgggcgg      6660
gtttcccggt gggcgtcggc aagctcccac acgacgtttt cagcgaggga gggcgcgggc      6720
cggacagtca tgttatcgga gggggaggga agagcggatt ttatcgccca ggtgctcaca      6780
acttcgtatg tcacggcaac cggggcgctt ttttcgcgca gttccccgcc tgtcacatcc      6840
tcacagggtt cttgactctc cggcacgcta ttagggagag ggtggagcat gttgtagacg      6900
gtgcgcccgg ccttcgcgtc ggcgttcagg tcgcgccagt tccggcccca atcgtcatgc      6960
atcaggcgga catatcccgc cttcccttcc agcacgcgcc tcggcttgag cgtcacggcc      7020
cacagcgtcc cggttgccac agactcgccg cgcaggtcgc ccatgtgggc atcacaggcc      7080
accagcccga cccggcgcag atattgaagg ttcacgtaga aggcggactt cttcagaccc      7140
acatgcacca tgagcagctc ggcgggcagg tggaacacag cgcgggtgac gtgttccgca      7200
tagccgcagg cgcgggccac gtccagcgcc accgagaaca gggcgcggaa gatgcgccgg      7260
gccgactcgc ggcaggggc gtcatctagg ctggcggtga gggtctgcac cagttcggcg      7320
cgtgtggcga tggtcaacgg cgcggcgcg ggctgggact gctgggcgat ggtgggcacg      7380
ggcggcggcg agatggaccg ggccgagctg gaaatttccc gtgtgagcgc aggtttaggc      7440
gcatggttac cttcctgcag tgaaatctgc gaaatcaggc ccgcttcgag gagtcggacc      7500
atgaatggat tgtgtctcaa gaaaaaagcc tcccctcttg tcagagggga gggtcccggt      7560
ctaccatgct ctcagcgacg agatagctgg ggtttgtgac cctgcactct gacaaagccc      7620
tcaccgaaag gtgggggttt agtcatttgg cctagtaaag cagaacagag gcgatttgtc      7680
acgcaaaggc ccgccgcccg aggggaaaca ggcggcgggc caatggctcg gcgttgttag      7740
```

```
ctggggtcg caccagggaa gcacagaagc ccttccctga gcagggtttc accgtgtggt    7800
gtcccttcgt ccttgaaggc gaactggtag gccaggccgt aatgctcctg caccatcttt    7860
tgctcatcca ccgcgacaaa gaaacggcgg gtgttcgccg ggctgctgag gtctgccac     7920 tcgccggacg cgcccaccgc ataggcgtct ccggctccac attcctcggc ctgctgatac    7980
tgatacttcg tccacagcat caccgcctta tcgggcacct gcgcgaagct caccagcgcc    8040
ccgaaccgcc cggcgctcgt ggtgaaggtg gacgactgca ccatgtcgga cagttccagc    8100
gtggcaggcg cgggcgtgtt cgtcggcgcg tacaccgtcc ccgcctcgca cacgaccagc    8160
ggggcggccc ccgtgccgaa ctcggcgcg ctgccgtttg ccagcgtgag cgccgaagac     8220
gccaccgcgc aggtacccat gggtgccgac caccagcagg tccacgccgt cgccgcctc    8280 ggtgagcacc tcgattggac ggcccctcag ggtctgaacc ctcccctgca cgcccgcctc    8340
cccgatgagt gtctgcgccg tctgctgcgc ctgccgggca ttctgctcca gcatctcccg    8400
gacgtagtcg ggattcagtc ccgcccactg aacgaagccg ctgaccggcg gctcctcgat    8460
cacagtcacg acctccagct cggcgcctgc cgccttcccg agcgttatgg cctgcttcaa    8520
ggcgcgctgg ctgggctcac ttccgtcaaa ggccaccacg aatcgcatcc gtcctcctcc    8580
ctgaccagtc aggttcagca agcagggtaa gcctctccca gcactccggg gcttcacacg    8640
gccttgggtc ttttctgcat acccatgagc tcagtacccg acagtttccg gcagggcttg    8700
aaaaagttcg gctgacacgc gagaactgga gcgcgtcccc gatgtcctgg ccaagttgac    8760
ccgctgcttc accgcgcact tcccggagtt ccgcaagaac taggtcgagc tgctctccct    8820
catggtcctc gccctcctta ggggcaagga cgtccggcat gctaaactcg ccgcgcgctt    8880
ccccggaagc gcgcacaccg cctccgtcat ccggcgggtg gaacgcttct tcgaccgtca    8940
tcctcttcgg ccagctgatg tcgcccgggt cgttctgacg ctccttcccg ccgcgcagcc    9000
acgcgaattt atccttgacc ggaccaactg gaagtatggg cagacggacg tgaacgtctt    9060
gttgctggcc gtcatttggc gggacgtcgc catccccctg ctctacgagt tgctgccca    9120 tgggggcagc agcgacaccg agattcggca caccctgatg gacgatgccc tgtgcctgct    9180
gtccgccgct gacatccggg tgctgtatgc cgaccgcgaa ttccacgcaa ctggtccaga    9240
accttgaccg aacgcagcgg tggtaacggc gcagtggcgg ttttcatggc ttgttatgac    9300
tgtttttttg gggtacagtc tatgcctcgg gcatccaagc agcaagcgcg ttacgccgtg    9360
ggtcgatgtt tgatgttatg gagcagcaac gatgttacgc agcagggcag tcgccctaaa    9420
acaaagttaa acatcatgag ggaagcggtg atcgccgaag tatcgactca actatcagag    9480
gtagttggcg tcatcgagcg ccatctcgaa ccgacgttgc tggccgtaca tttgtacggc    9540
tccgcagtgg atggcggcct gaagccacac agtgatattg atttgctggt tacggtgacc    9600
gtaaggcttg atgaaacaac gcggcgagct ttgatcaacg accttttgga aacttcggct    9660
tcccctggag agagcgagat tctccgcgct gtagaagtca ccattgttgt gcacgacgac    9720
atcattccgt ggcgttatcc agctaagcgc gaactgcaat ttggagaatg gcagcgcaat    9780
gacattcttg caggtatctt cgagccagcc acgatcgaca ttgatctggc tatcttgctg    9840 acaaagcaa gagaacatag cgttgccttg gtaggtccag cggcggagga actctttgat    9900
ccggttcctg aacaggatct atttgaggcg ctaaatgaaa ccttaacgct atggaactcg    9960
ccgcccgact gggctggcga tgagcgaaat gtagtgctta cgttgtcccg catttggtac   10020
agcgcagtaa ccggcaaaat cgcgccgaag gatgtcgctg ccgactgggc aatggagcgc   10080
ctgccggccc agtatcagcc cgtcatactt gaagctagac aggcttatct tggacaagaa   10140
```

<210> SEQ ID NO 22
<211> LENGTH: 1647
<212> TYPE: DNA
<213> ORGANISM: Artificial Sequence
<220> FEATURE:
<223> OTHER INFORMATION: Deinococcus radiodurans DNA sequence

<400> SEQUENCE: 22

```
gaagatcgct tggcctcgcg cgcagatcag ttggaagaat ttgtccacta cgtgaaaggc    10200
gagatcacca aggtagtcgg caaataa                                        10227
```

```
atgacatctg cacttcctcg ccctgctcct tcgccctatg cccgccgcaa gacggccctc      60
gtcatcggcg cgggcttcgg cggcctcgcg ctcggcattc ggctgcaaag cctaggcttc     120
gacaccacca ttctggaacg gctcgatgga ccgggggggtc gcgcctacca gaagcgcacg    180
ccggacgggt atgtgttcga catggggccg accgtgctga cggtgccgca tttcatcgag    240
gaactgttcg cgctggagcg ggaccgcgct ggcctgacg cgcccgacta cccacccgag     300
gtgctgagcg gcgagcgggt caaggagggc gtgagcggcg gcccccacac cagccggtac    360
gtgacgctgg tgccgatttt gcccttctac cgcatcgtct ttcatgacgg cacgtatttc    420
gactacgacg gcgacccgga gagcacccgg cgccagattg ccgaactcgc gccgggcgac    480
ctcgcgggct atgagcgctt tcacgccgac gccgaggcga ttttccggcg gggctttctg    540
gaactcggct acacccattt cggcgacgtg ccgacgatgc tgcgggtggt gccccgacctg    600
ctgaagctcg acgcggtgcg caccctcttt tcgttcacgt ctaaatactt ccagtcggac    660
aaactgcggc aggtcttttc cttcgagacg ctgctcgtcg gcggcaatcc gctgagcgtg    720
cccgccatct acgcgatgat tcacttcgtc gagaagacct ggggcatcca ctacgcgatg    780
ggcggcaccg gggcgctggt gcgcgggctg gtgcagaaat ttgaggagct cggcggagcc    840
atccgctacg gcgccggcgt agacgaggtg ctggtggacg gcaatctacc cggcaaacgc    900
acagcgcgcg gtgtgcggct ggagagcggc gaagagctgc gggccgacct ggtggcgagc    960
aacggcgact gggcgaacac ctacctcaag cgcgtgcgtc cctcggcgcg gctggtcaat   1020
tcggacctgc gggtgaaggc cgccagcgaa agcatgagcc tgctcgtcgt ctatttcggc   1080
tttcgcggcg gcgacgatct gccgctcaag caccacaaca tcctgctggg gccgcgctac   1140
gaggcgctgc tgagcgagat tttcgggacc aagcggctcg gcgaggattt cagccagtac   1200
ctgcatgtgc ccacgctgac cgaccccgcg ctggccccccg ccgggcacca gccgcctac    1260
acgctggtgc cggtgcccca caacggcagc ggcatcgact gggacgtgga agggccaaag   1320
ctggccgaag ctgccctggc cgacatcgaa cggcgcggcc tgattccggg gctgcgtgag   1380
cgcctgaccc acttcgagtt catcacgccc gactacttcg cgggcacgct cgacagctac   1440
ctcggcaacg ccttcgggcc ggagccacgg cttgtccaga gcgcttttt ccgcccgcac    1500
aaccgcagcg aggacctgca caacttctac ctcgtcggcg cgggcgcgca gccgggcgcc   1560
gggacgccga gcgtgatgat gtcggccaag atgacggccc gcctgatcgc cgaggacttc   1620
gggattcacg cggacatccg cgcgctga                                      1647
```

<210> SEQ ID NO 23
<211> LENGTH: 29
<212> TYPE: DNA
<213> ORGANISM: Artificial Sequence
<220> FEATURE:
<223> OTHER INFORMATION: dr0862F1 DNA sequence

<400> SEQUENCE: 23
aagtactagt atgaggtcta gggccggtt                          29

<210> SEQ ID NO 24
<211> LENGTH: 32
<212> TYPE: DNA
<213> ORGANISM: Artificial Sequence
<220> FEATURE:
<223> OTHER INFORMATION: dr0862R1 DNA sequence

<400> SEQUENCE: 24
ctatgcggcc gctcagccgt ggaccgcgcc ca                      32

<210> SEQ ID NO 25
<211> LENGTH: 30
<212> TYPE: DNA
<213> ORGANISM: Artificial Sequence
<220> FEATURE:
<223> OTHER INFORMATION: dr1087F1 DNA sequence

<400> SEQUENCE: 25
gttaactagt atgcggctgg acactgtgtt                         30

<210> SEQ ID NO 26
<211> LENGTH: 32
<212> TYPE: DNA
<213> ORGANISM: Artificial Sequence
<220> FEATURE:
<223> OTHER INFORMATION: dr1087R1 DNA sequence

<400> SEQUENCE: 26
ctaggcggcc gccttgcaga ggggtccctt ta                      32

<210> SEQ ID NO 27
<211> LENGTH: 30
<212> TYPE: DNA
<213> ORGANISM: Artificial Sequence
<220> FEATURE:
<223> OTHER INFORMATION: dr1395F1 DNA sequence

<400> SEQUENCE: 27
aagtactagt atgcgtcccg aactgctcgc                         30

<210> SEQ ID NO 28
<211> LENGTH: 32
<212> TYPE: DNA
<213> ORGANISM: Artificial Sequence
<220> FEATURE:
<223> OTHER INFORMATION: dr1395R1 DNA sequence

<400> SEQUENCE: 28
ataggcggcc gctcacttct cccgcgtcgc ca                      32

<210> SEQ ID NO 29
<211> LENGTH: 30
<212> TYPE: DNA
<213> ORGANISM: Artificial Sequence
<220> FEATURE:
<223> OTHER INFORMATION: dr1475F1 DNA sequence

<400> SEQUENCE: 29
ctagactagt gtgaacgaac ttcccggcac                         30

<210> SEQ ID NO 30
<211> LENGTH: 32

<212> TYPE: DNA
<213> ORGANISM: Artificial Sequence
<220> FEATURE:
<223> OTHER INFORMATION: dr1475R1 DNA sequence

<400> SEQUENCE: 30
taacgcggcc gcctacacct caatcggcac gt                                    32

<210> SEQ ID NO 31
<211> LENGTH: 32
<212> TYPE: DNA
<213> ORGANISM: Artificial Sequence
<220> FEATURE:
<223> OTHER INFORMATION: groF DNA sequence

<400> SEQUENCE: 31
ataggcggcc gctcggcttg gaagcacgta tt                                    32

<210> SEQ ID NO 32
<211> LENGTH: 30
<212> TYPE: DNA
<213> ORGANISM: Artificial Sequence
<220> FEATURE:
<223> OTHER INFORMATION: dr1087R2 DNA sequence

<400> SEQUENCE: 32
gttacctagg cttgcagagg ggtcccttta                                       30

<210> SEQ ID NO 33
<211> LENGTH: 42
<212> TYPE: DNA
<213> ORGANISM: Artificial Sequence
<220> FEATURE:
<223> OTHER INFORMATION: dr1395R2 DNA sequence

<400> SEQUENCE: 33
ctaggtcgac cttaagccta ggtcacttct cccgcgtcgc ca                         42

<210> SEQ ID NO 34
<211> LENGTH: 30
<212> TYPE: DNA
<213> ORGANISM: Artificial Sequence
<220> FEATURE:
<223> OTHER INFORMATION: dr1475R2 DNA sequence

<400> SEQUENCE: 34
gttacctagg ctacacctca atcggcacgt                                       30

<210> SEQ ID NO 35
<211> LENGTH: 20
<212> TYPE: DNA
<213> ORGANISM: Artificial Sequence
<220> FEATURE:
<223> OTHER INFORMATION: dr2250-1 DNA sequence

<400> SEQUENCE: 35
catgttcatc accagccgca                                                  20

<210> SEQ ID NO 36
<211> LENGTH: 40
<212> TYPE: DNA
<213> ORGANISM: Artificial Sequence
<220> FEATURE:
<223> OTHER INFORMATION: dr2250-2 DNA sequence

<400> SEQUENCE: 36

<210> SEQ ID NO 37
<211> LENGTH: 40
<212> TYPE: DNA
<213> ORGANISM: Artificial Sequence
<220> FEATURE:
<223> OTHER INFORMATION: dr2250-3 DNA sequence

<400> SEQUENCE: 37
gtgatactgc tcccgctaca gtcgacggta tcgataagct                    40

<210> SEQ ID NO 38
<211> LENGTH: 40
<212> TYPE: DNA
<213> ORGANISM: Artificial Sequence
<220> FEATURE:
<223> OTHER INFORMATION: dr2250-4 DNA sequence

<400> SEQUENCE: 38
aatgccttct cgccatccag catgcctgca ggtcgactct                    40

<210> SEQ ID NO 39
<211> LENGTH: 40
<212> TYPE: DNA
<213> ORGANISM: Artificial Sequence
<220> FEATURE:
<223> OTHER INFORMATION: dr2250-5 DNA sequence

<400> SEQUENCE: 39
agagtcgacc tgcaggcatg ctggatggcg agaaggcatt                    40

<210> SEQ ID NO 40
<211> LENGTH: 20
<212> TYPE: DNA
<213> ORGANISM: Artificial Sequence
<220> FEATURE:
<223> OTHER INFORMATION: dr2250-6 DNA sequence

<400> SEQUENCE: 40
gatgtcgcga gttcgaatct                                         20

<210> SEQ ID NO 41
<211> LENGTH: 978
<212> TYPE: DNA
<213> ORGANISM: Deinococcus radiodurans

<400> SEQUENCE: 41
gtgaggtcta gggccggttt gtctcttaga ctgccgacga ggaccctcac cgtgacggac    60
tattcacctg ccctgccctg caccgaactg cgccgcccgc cgctggcgca ggcagtgagg   120
tactgccggg acctgacgcg gcagcacagc aagacgtttt atctggggtc gcaactgttt   180
tcgccacccg agcgggccgc cgtgtgggcg gtctacgccg cctgccgcgc cggggacgac   240
atcgtggacg aggcgggaaa cggggaccgc gagcgcgaac tccgtgagtg gcgcagccgg   300
attgacgcgg cgtttgcggg gcaaccggcg gacgacccca tcagcacggc gctggcgtgg   360
gcggcggggc gctacgccat tccccacagc gcctttgccg agctgcacga gggcctgaac   420
atggacctgc gtgggcacga gtaccgcgac atggacgacc tgttgctcta ctgccgccgg   480
gtggccgggg tggtgggggtt catggtcgcg cctatcagcg gctaccgggg cggcgcggcg   540
acgctgaacg acgccttgca actcggtcag gcgatgcagc tcaccaacat cctgcgcgac   600
gtgggcgagg acctgacgcg cggacgggtc tacctgccgc agagcctgct cgacgaatac   660

```
ggcctgtcac gcgccgcgct ggagcgctgg ggccagggcg aaccgctcag ccccgcctac    720
cgcgccctga tgacgcacct cggcgggctg gcgcgcgagt ggtacgccgc tggccgcgcc    780
gggattccgc agctcgacgg acgcggcccg ctggcggtgc tgaccgccgc ccgcgcctac    840
gagggcattc tggacgacct cgaacgcgcc ggctacgaca atttcgggcg ccgcgcctac    900
gtgagtggcc ggcgcaaact gctgatgctg ccgcaggcgt ggtgggaact gcgctcgctg    960
ggcgcggtcc acggctga                                                  978

<210> SEQ ID NO 42
<211> LENGTH: 861
<212> TYPE: DNA
<213> ORGANISM: Deinococcus radiodurans

<400> SEQUENCE: 42
atgcggctgg acactgtgtt tctgggccgc cgcctgaaag ccccggtgct catcggcgcc    60
atgactggcg gggccgagaa agcgggcgtc atcaaccgca acctcgccac cgccgcccgt    120
aacctcggcc tggggatgat gctcggctcg cagcgggtca tgctggaaca ccccgacgcc    180
tgggaatcgt tcaacgtgcg cgaggtggct cccgagattc tgctcatcgg caacctcggc    240
gcggcgcagt ttatgctcgg gtacggagcc gagcaggccc ggcgcgcggt ggacgaggtg    300
atggccgacg cgctcgccat tcacctcaac ccgctgcaag aagccctgca acgcggcggc    360
gacacccgct ggcagggcgt gacttaccgg ctcaaacagg tggcgcgcga actggatttc    420
cccgtcatca tcaaggaagt cgggcacggg ctggacgcgg cgacgctgcg ggccctcgcc    480
gacggcccct ttgccgccta cgacgtggcg ggcgcgggag gcacgagctg ggcgcgggtc    540
gaacaactcg tcgcgcacgg gcaggtgcac tcccccgacc tctgcgaact cggagtgccc    600
accgcgcagg cgctccggca agcgcgcaaa acgctgccgg gggcgcagct catcgcttcc    660
ggcggcatcc gcagcggtct ggatgctgcc cgcgccctgt cgctggggge cgaggtggtg    720 gcggtggccc ggcccctgct ggagcccgcg ctggacagca gtgaggcggc ggaagcgtgg    780
ctgcggaact ttattcagga attacgggtg gcgctgttcg tgggcggcta ccgggacgtg    840
cgggaggtgc gggggggta a                                              861

<210> SEQ ID NO 43
<211> LENGTH: 990
<212> TYPE: DNA
<213> ORGANISM: Deinococcus radiodurans

<400> SEQUENCE: 43
atgcgtcccg aactgctcgc ccgcgtgctc tcgctgctgc ccgaaaccag cgccacgccc    60
gaactcgccc gcttctacgc gctgctgcgc gactacccgc agcgcggcgg caagggcatc    120
cgctcggagc tgctgctcgc cagcgcccgc gcccacggcc tgagcgagtc ggacaccggg    180
tgggagagcg ccctgtggct cgccgccgcg ctggaactgt ttcagaactg ggtgctggtc    240
cacgacgaca tcgaggacga ctccgaggag cgccggggcc ggcccgcgct gcaccacctg    300
tgcgggatgc cggtggcgct caacgtgggc gacgcgctgc acgcctatat gtggcggcg    360 gtgggcaaag cgaacgtgcc cggcgctttc gaggaattct tgcagatggt ttaccgcacc    420
gccgaggggc agcacctcga cctcgcctgg gtggagggcc gcgagtgggg gctgcggccc    480
gccgactacc tgcaaatggt gggcctgaaa accgcgcact acacggtgat cgtgccgctg    540
cggctggggg cattggcggc aggcatggcg ccgcaggacg ctttaccccc ggcgggactg    600
```

```
gcactcggca ccgccttcca gattcgggac gacgtgctca acctcgcggg cgacccggtg    660
aaatatggca aggaaatcgg cggcgacttg ctcgaaggca agcgcaccct gatcgtgctg    720
gactggctga ccaccgcacc cgacgaccgg aaggcgattt ttctcgacca gatgcgccgg    780
caccgcgccg acaaggaccc cgccgtcatt gacgagattc accgctggct gctggaaagc    840
ggcagcgtgg aagccgcgca ggactacgcg caggcgcagg ctgccgaggg gctggacctg    900
ctggaaaaag cgttggcaga cgccccggac gcgcaggccg ccgccgcact gctcgccagc    960
gtacgcgaac tggcgacgcg ggagaagtga                                    990
```

<210> SEQ ID NO 44
<211> LENGTH: 1890
<212> TYPE: DNA
<213> ORGANISM: Deinococcus radiodurans

<400> SEQUENCE: 44

```
gtgaacgaac ttcccggcac gtccgatacc ccgctgctcg accagattca tggccccaaa     60
gacctcaaac gcctctcgcg ggagcagttg cccgcgctga ccgaggagct gcgcggcgaa    120
atcgtgcgtg tctgctcgcg cggcggcctg cacctcgcgt cctcgctcgg cgcggtggac    180
atcatcacgg cgctgcatta cgtgctcgac tcgccgcgcg accggattct cttcgacgtg    240
gggcatcagg cctacgccca caaaatcctg accgggcggc gcgaccagat ggccgacatc    300
aagaaagaag cggcatcag cggctttacc aaggtttccg agtccgaaca cgacgcgatt    360
acggtgggcc acgcctccac ctccctcgcc aacgcgctcg gcatggcgct cgcgcgtgac    420
gcgcagggca aggatttcca cgtcgctgcc gtcatcggcg acggctcgct gaccggcggg    480
atggccctcg ccgcgctcaa caccatcggc gacatgggcc gcaagatgct gatcgtgctc    540
aacgacaacg agatgagcat ctcggaaaat gtcggggcca tgaacaaatt catgcgcggg    600
ctgcaagtcc agaagtggtt tcaggaaggc gaaggtgcgg gcaaaaaagc ggtggaagcc    660
gtcagcaagc cgctcgccga cttcatgagc cgggcgaaaa actccacccg ccacttcttc    720
gaccccgcca gcgtcaaccc cttcgccgcg atgggcgtgc gctacgtcgg cccggtggac    780
ggccacaacg tgcaggaact ggtgtggctg ctcgaaagac tggtggacct cgatggcccg    840
accatcctcc acatcgtcac caccaagggc aagggcctga gctacgccga ggccgacccg    900
atctactggc acgccccggc caagttcgac ccggcgaccg gcgagtacgt gccgagcagc    960
gcctattcgt ggagcgccgc cttcggtgag gccgtgaccg agtgggcgaa gaccgacccg   1020
cgcaccttcg tcgtcacgcc cgccatgcgc gagggcagcg ggctggtcga attcagccgc   1080
gtacacccgc accgttacct cgacgtgggc atcgccgagg aagtcgcggt gacgacggcg   1140
gcgggcatgg cgctgcaagg gatgcggccc gtcgtcgcca tctactccac cttcctgcaa   1200
cgcgcctacg accaggtgtt gcacgacgtg gcgattgagc acctcaacgt caccttctgc   1260
atcgaccgcg cgggcatcgt gggggcggac ggggccacgc acaacggcgt gttcgacctc   1320
agcttcctgc gctctatccc cggcgtccgc atcgggctgc cgaaagacgc cgccgaactg   1380
cgcgggatgc tcaagtacgc ccagacgcac gacggcccct ttgccatccg ctacccgcgc   1440
ggcaatacgg cgcaggtgcc cgccgggacg tggccggacc tgaaatgggg cgagtgggaa   1500
cggctgaagg ggggcgacga cgtggtgatt ctggcgggcg gcaaggcgct cgactatgcc   1560
ttgaaggccg ccgaggacct ccccggtgtg gcgtggtca atgccgcctt cgtcaagccg   1620
ctcgacgaag agatgctgcg cgaggtgggg ggccgggccc gcgccctgat tacggtggaa   1680
gacaacaccg tcgtcggcgg cttcggggc gcggtgctcg aggcgctgaa cagcatgaac   1740
```

```
ctgcatccca ccgtgcgcgt tctcggcatt cccgacgagt tcaggaaca cgccactgcc      1800 gagagcgtcc acgcccgcgc cggcatcgac gccccggcga ttcggacggt gctcgccgaa      1860
ctcggggtgg acgtgccgat tgaggtgtag                                      1890

<210> SEQ ID NO 45
<211> LENGTH: 1473
<212> TYPE: DNA
<213> ORGANISM: Deinococcus radiodurans

<400> SEQUENCE: 45
gtgatactgc tcccgctaca ctgcggccat gtgccctgtt tccctcccct ggagctgcct        60
gtgacccatg tggcggtgat cggggccggt ttctcagggc tggcggcggc cctgcggctg       120
gcccaggcag gggcgcaagt gacggtgctc gatgccctcg accggcccgg cggcaaggcg       180
gcgctcgggt acgacgattt ctccagcggg cccaccgtcg tcaccatgcc gcagattttc       240
gccgcgctgc acgcccgtct cggctgggac gctcccgcgc tgaccccggc gcaccccacc       300
accacgtacc acgcgctgag cgggcggaca tttgctcccg aggccctcaa cgtggtcggc       360
agtcttgacc ctaccatgac ccagcttttcc cgcgcagaag ggcgacgtta ccgccaactc       420
ctgttcgctg cccggcagat gtacagcggc gcggcggata ccttccttttt cgcgccaccg       480 cccacccgca cgcagctcgc ccagtacgcg ctccgggctg ggcggcaggc ggcgccgctg       540
accccactgg cccggtacgt gcgctcggga ccgtttctca cgccgttctg gctgcgcttc       600
gccacctacc ttggggccga tccttaccgt gccccgccg tgctgcacaa catcgcctgg       660
gtcgaactgg gcgacggcat ctggcatctg cccggcggtc tgctcgccct cgccgagcgc       720
ctgtacgccg aagcactcga ccgtggcgtg cgcttcgaat tcggtattca ggtgcagcac       780
ctcagcaccc acggaggccg ggtcctgggg gctcacacca gccgggggc cttcgccgct       840 gaccgctggg tcagtgccgc cgaccgcgct ctgactctgg gatggctggg ccaggacaca       900
ccgaccacgc cccgaggcgt cagcggcttt gccctacaac tgcgcctggg cgaagacctg       960
gggcaaggtc accacatctt ctggcctgcc gactacgccc gcgagtggca ggacattcgc      1020
gcgggtcgcc tgccgagcga gccgactctt tacctgcacc tcgacggccc ccgcgccttc      1080
ctgctcgtta atgcgccgcc cgacccccgc ctgggccttt cccctgagcg caaagccgac      1140
tacgcccgtc accttttgca acggttgcaa agccgctttc ctctgcctgt ggtggagtgg      1200
caagctcttg cccctgcgga ttacgcccgt accgggctgg gggtgcgct gtatggccgg      1260 gcacctcacg gcctgctcgg cagcctgcgc cccggctggc ggctcccgca ggcccgcaat      1320
ctcgttcagg tgggcgggac cgttcaccct ggcggcggcg ttccactgtc actcctctcc      1380
ggctggaacg gggcaggcag tttgcttgga ttggactacg actccctgga tggcgagaag      1440
gcatttggaa agcccgctcc agccatcaaa taa                                  1473
```